United States Patent
Cribier

(10) Patent No.: US 6,908,481 B2
(45) Date of Patent: Jun. 21, 2005

(54) VALUE PROSTHESIS FOR IMPLANTATION IN BODY CHANNELS

(75) Inventor: Alain Cribier, Maromme (FR)

(73) Assignee: Edwards Lifesciences PVT, Inc., Irvine, CA (US)

(*) Notice: Subject to any disclaimer, the term of this patent is extended or adjusted under 35 U.S.C. 154(b) by 0 days.

(21) Appl. No.: 10/139,741

(22) Filed: May 2, 2002

(65) Prior Publication Data

US 2003/0014104 A1 Jan. 16, 2003

Related U.S. Application Data

(63) Continuation of application No. 09/795,803, filed on Feb. 28, 2001, now abandoned, which is a continuation of application No. 09/345,824, filed as application No. PCT/EP97/07337 on Dec. 31, 1997, now abandoned.

(30) Foreign Application Priority Data

Dec. 31, 1996 (EP) .............................................. 96402929

(51) Int. Cl.[7] .................................................. A61F 2/24
(52) U.S. Cl. ...................................... 623/2.11; 623/904
(58) Field of Search ............................. 623/1.11, 1.24, 623/1.26, 2.11, 904, 900; 606/191, 192, 194

(56) References Cited

U.S. PATENT DOCUMENTS

| | | |
|---|---|---|
| 3,548,417 A | 12/1970 | Kisher |
| 3,657,744 A | 4/1972 | Ersek |
| 4,265,694 A | 5/1981 | Boretos et al. |
| 4,373,216 A | 2/1983 | Klawitter |
| 4,406,022 A | 9/1983 | Roy |
| 4,535,483 A | 8/1985 | Klawitter et al. |
| 4,605,407 A | 8/1986 | Black et al. |
| 4,643,732 A | 2/1987 | Pietsch et al. |
| 4,692,164 A | 9/1987 | Dzemeshkevich et al. |
| 4,759,758 A | 7/1988 | Gabbay |
| 4,829,990 A | 5/1989 | Thuroff et al. |
| 4,851,001 A | 7/1989 | Taheri |
| 5,032,128 A | 7/1991 | Alonso |
| 5,037,434 A | 8/1991 | Lane |
| 5,080,668 A | 1/1992 | Bolz et al. |
| 5,282,847 A | 2/1994 | Trescony et al. |
| 5,360,444 A | 11/1994 | Kusuhara |
| 5,411,552 A | 5/1995 | Andersen et al. |
| 5,500,014 A | 3/1996 | Quijano et al. |
| 5,545,214 A | 8/1996 | Stevens |
| 5,571,175 A | 11/1996 | Vanney et al. |
| 5,591,195 A | 1/1997 | Taheri et al. |
| 5,607,464 A | 3/1997 | Trescony et al. |
| 5,609,626 A | 3/1997 | Quijano et al. |
| 5,728,068 A | 3/1998 | Leone et al. |
| 5,749,890 A | 5/1998 | Shaknovich |
| 5,840,081 A | 11/1998 | Andersen et al. |
| 5,855,601 A | 1/1999 | Bessler et al. |
| 5,855,602 A | 1/1999 | Angell |
| 6,132,473 A | 10/2000 | Williams et al. |
| 6,454,799 B1 | 9/2002 | Schreck |
| 6,458,153 B1 | 10/2002 | Bailey et al. |

Primary Examiner—Brian E Pellegrino
(74) Attorney, Agent, or Firm—David L. Hauser; William H. Dippert

(57) ABSTRACT

A valve prosthesis which is especially useful in the case of aortic stenosis and capable of resisting the powerful recoil force and to stand the forceful balloon inflation performed to deploy the valve and to embed it in the aortic annulus, comprises a collapsible valvular structure and an expandable frame on which said valvular structure is mounted. The valvular structure is composed of physiologically compatible valvular tissue that is sufficiently supple and resistant to allow the valvular structure to be deformed from a closed state to an opened state. The valvular tissue forms a continuous surface and is provided with strut members that create stiffened zones which induce the valvular structure to follow a patterned movement in its expansion to its opened state and in its turning back to its closed state.

12 Claims, 18 Drawing Sheets

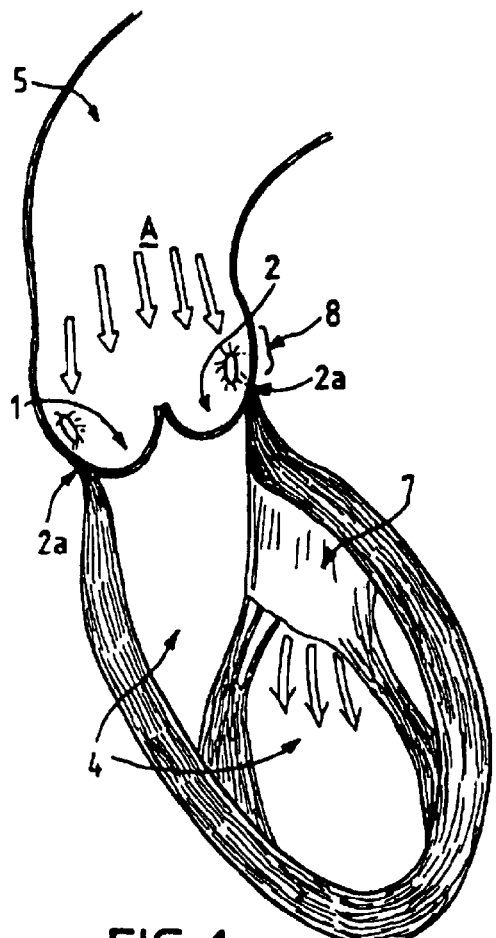
FIG_1a
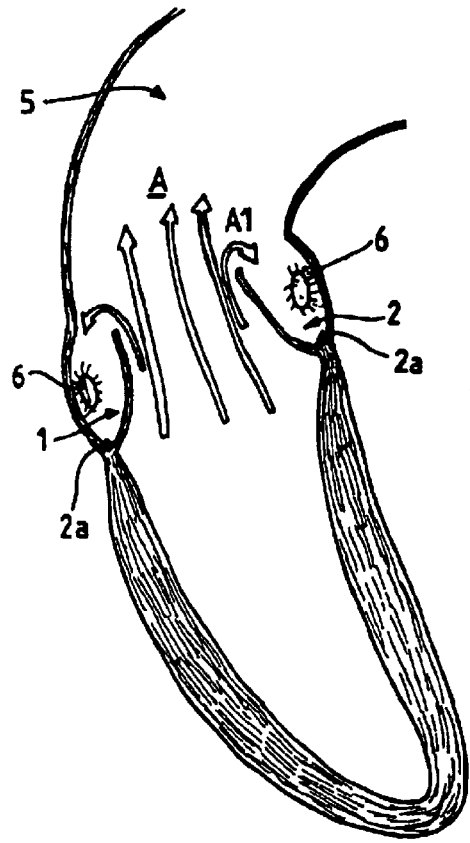
FIG_1b
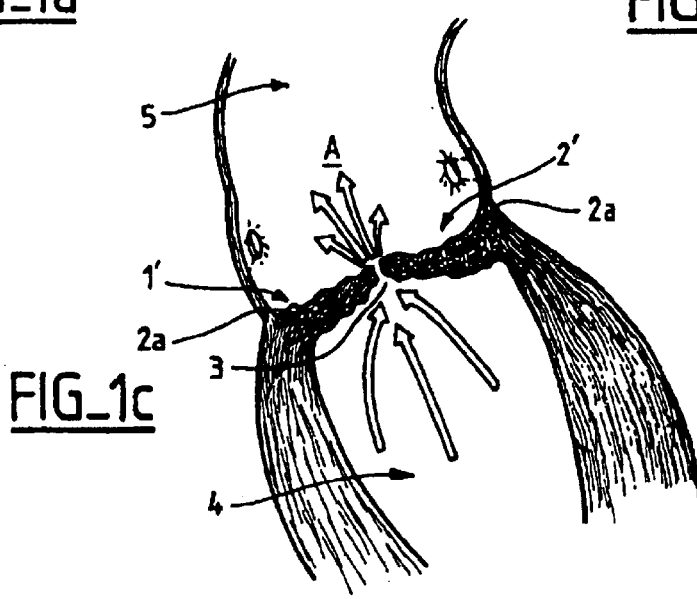
FIG_1c

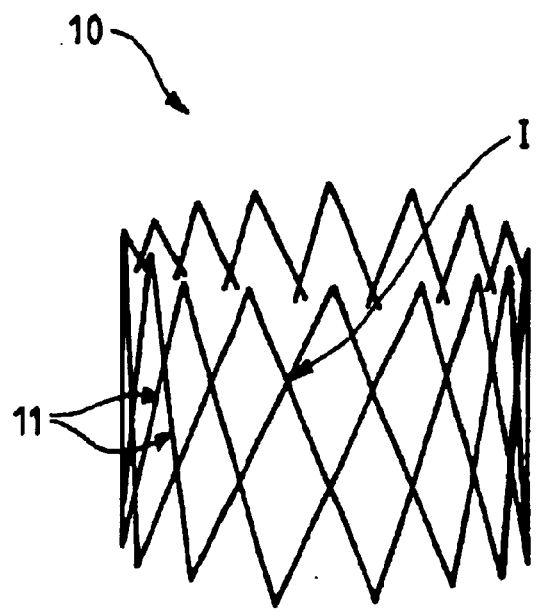
FIG_2a
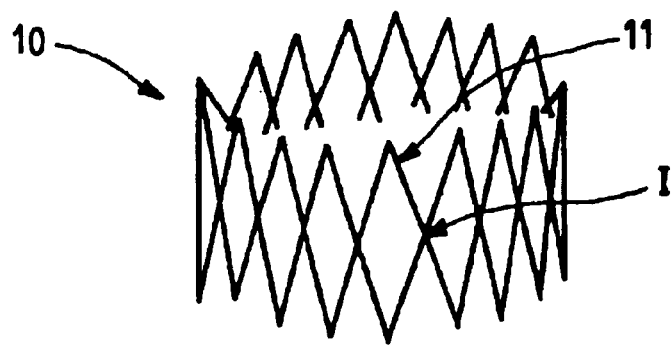
FIG_2b

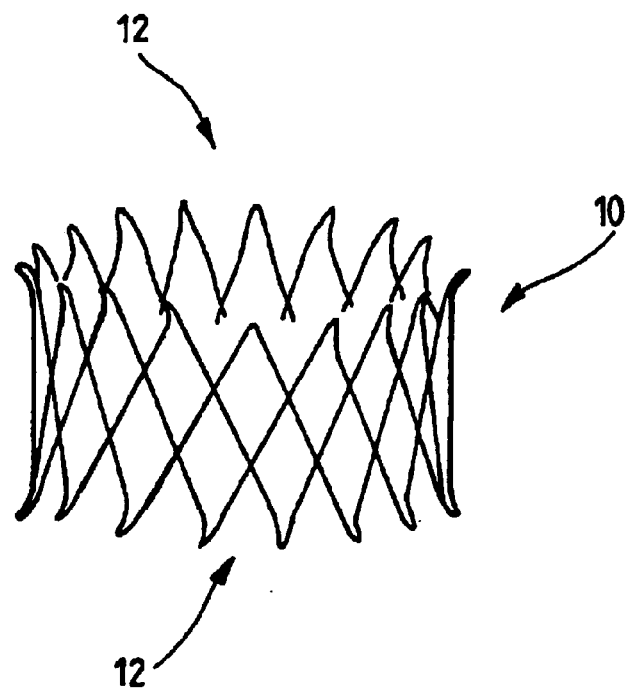
FIG_3a
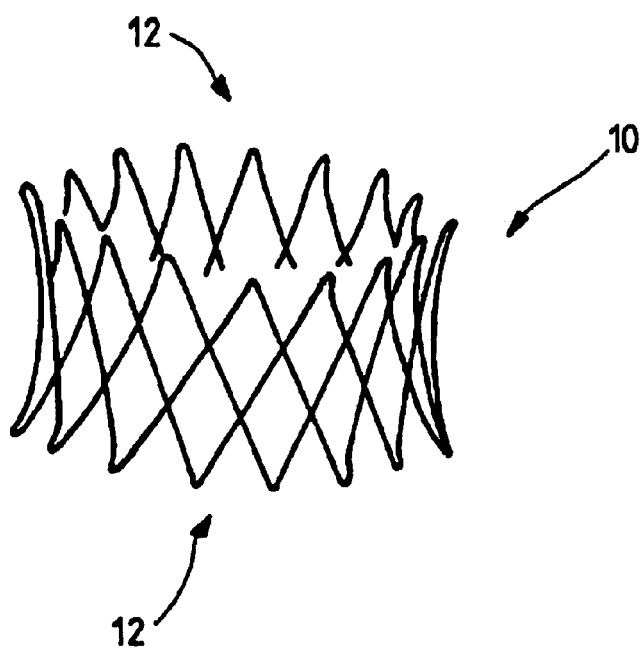
FIG_3b

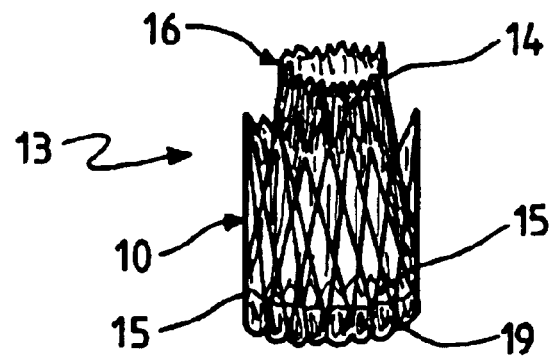
FIG_4a
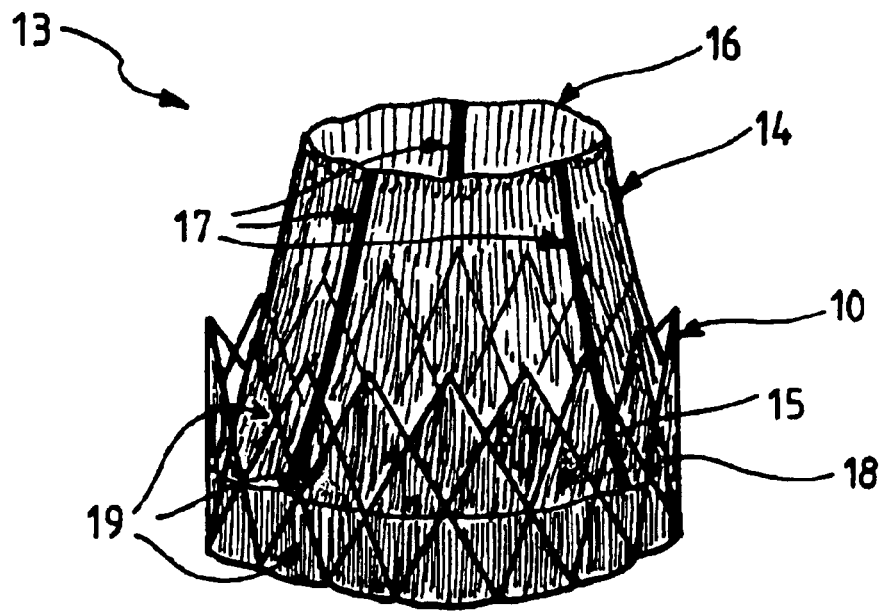
FIG_4b

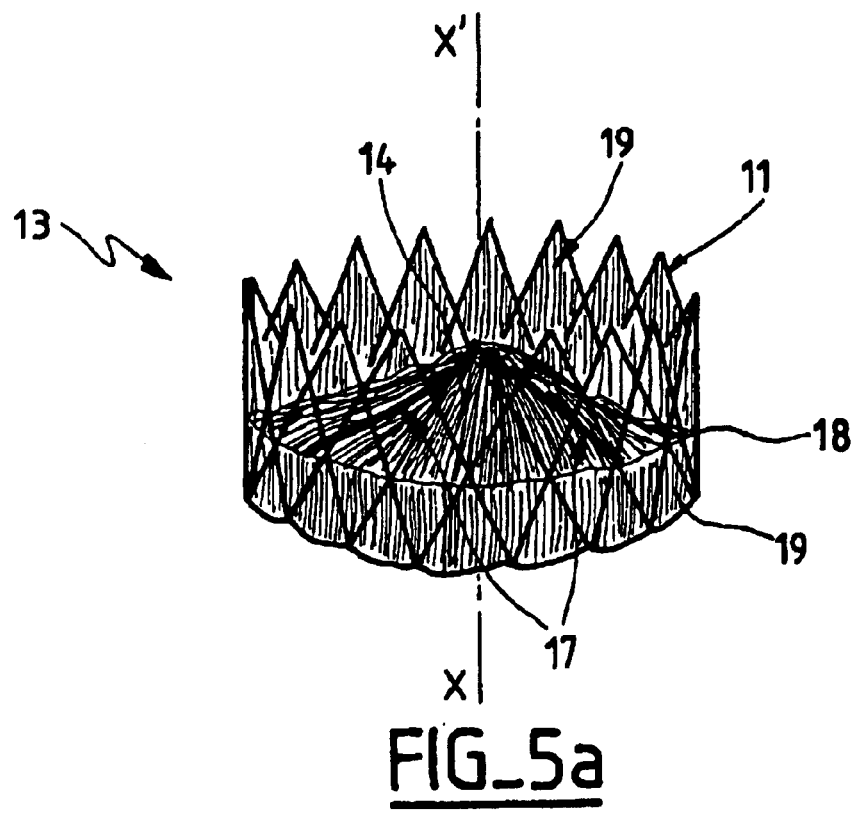
FIG_5a
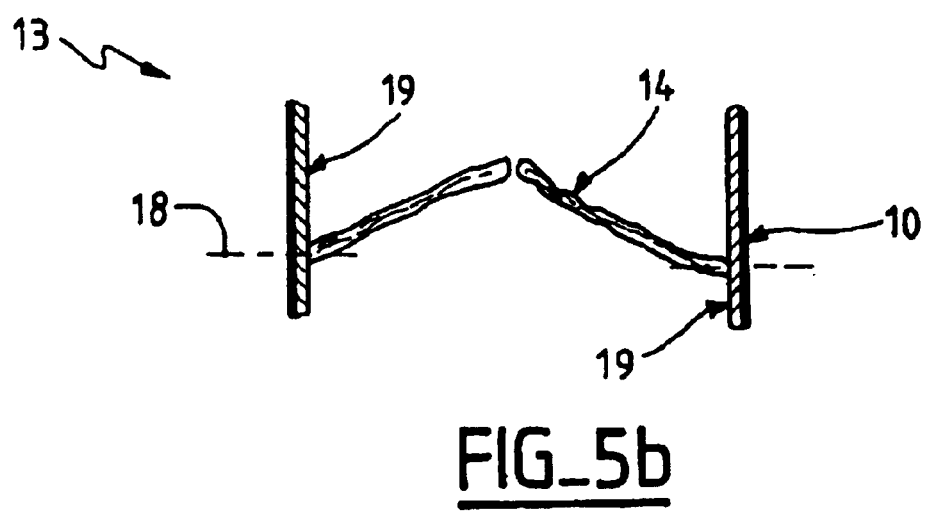
FIG_5b

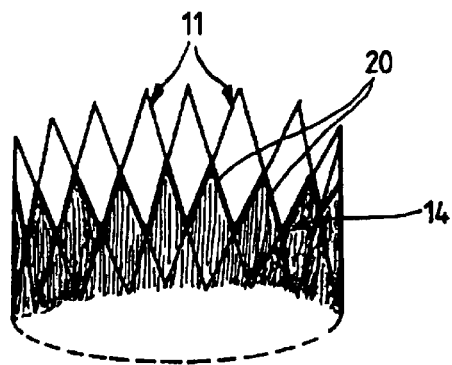
FIG_7
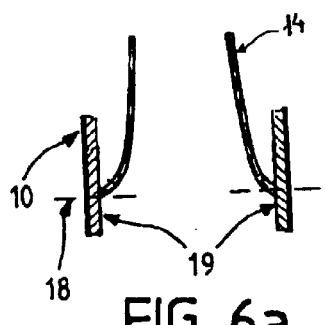
FIG_6a
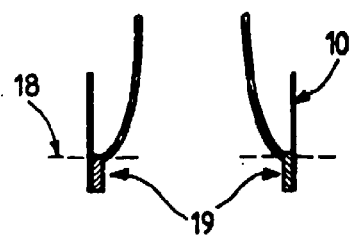
FIG_6b
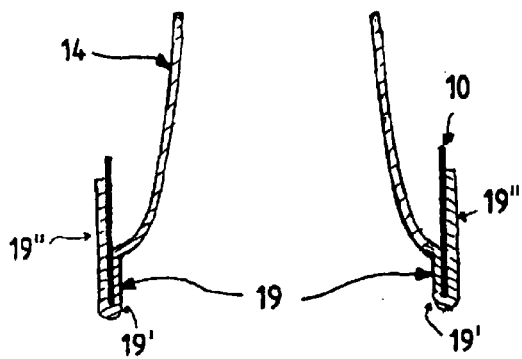
FIG_6d
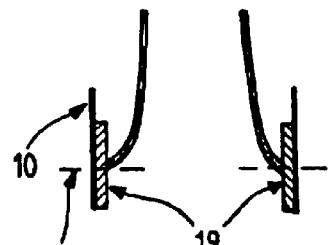
FIG_6c

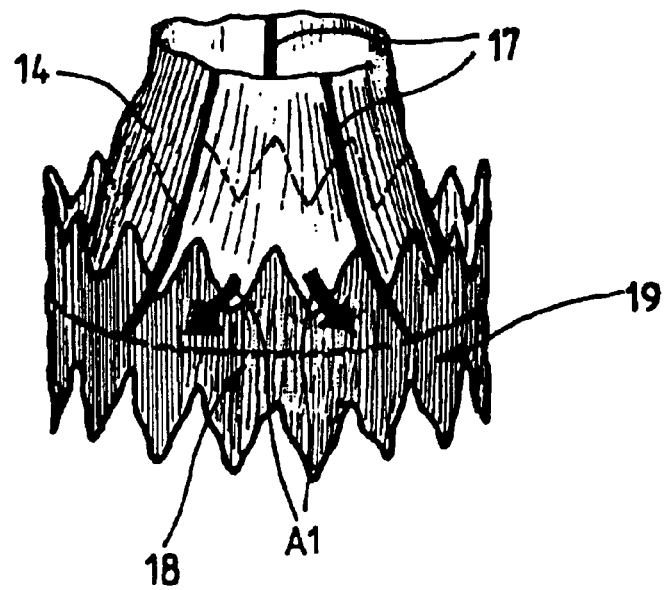
FIG_8a
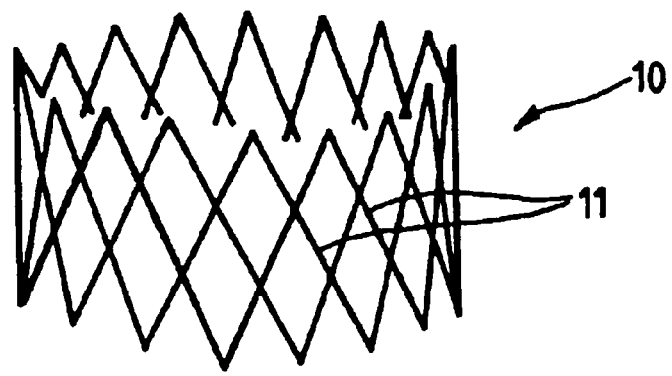
FIG_8b

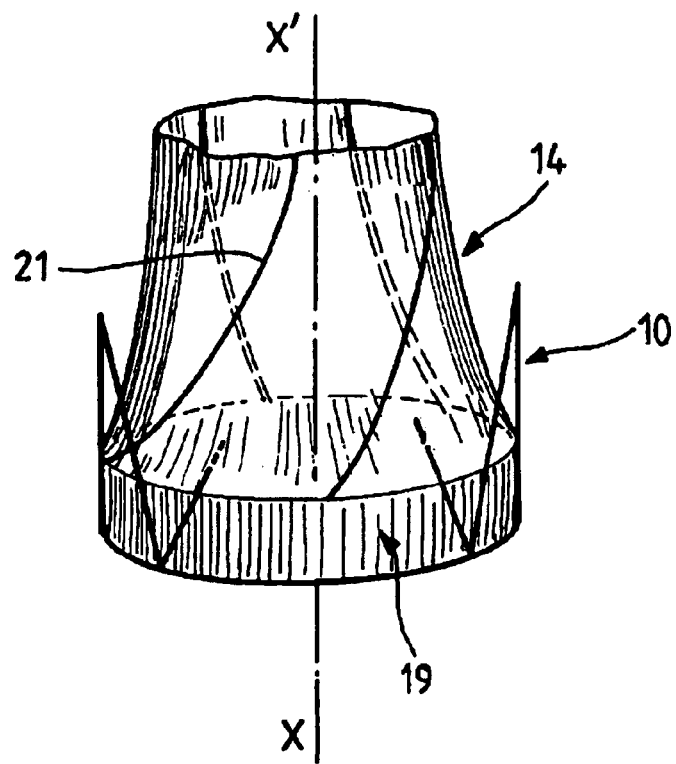
FIG_9a
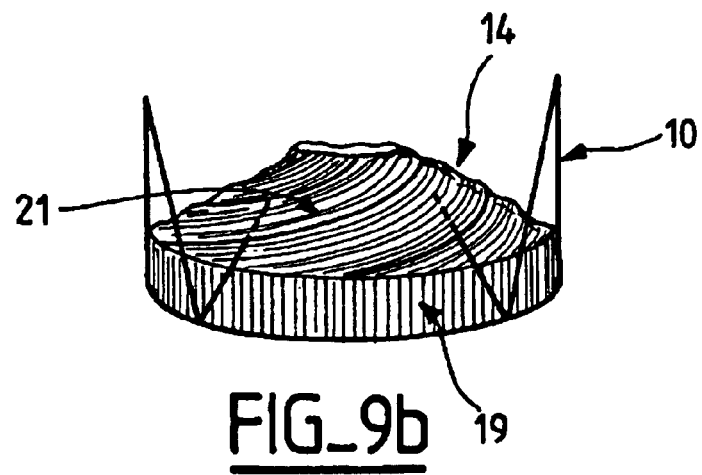
FIG_9b

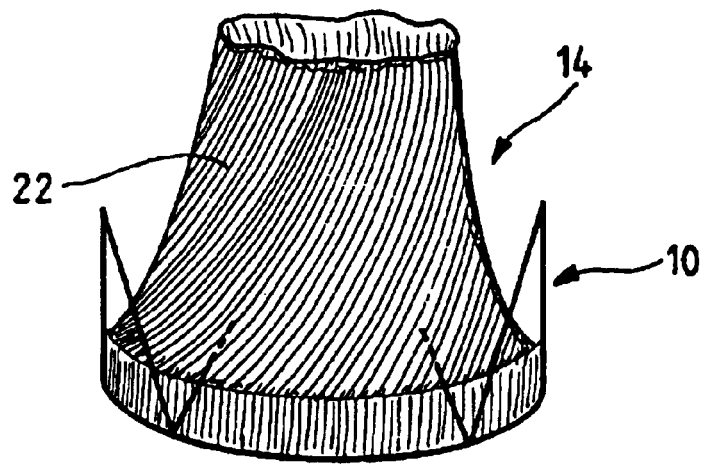
FIG_10a
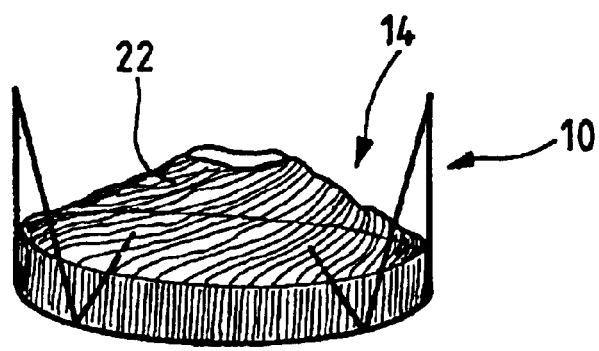
FIG_10b

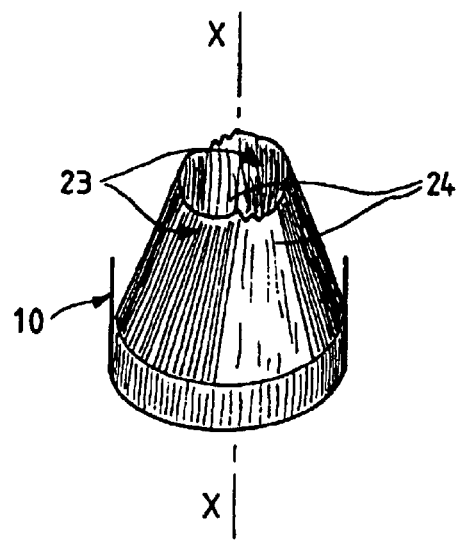
FIG_11a
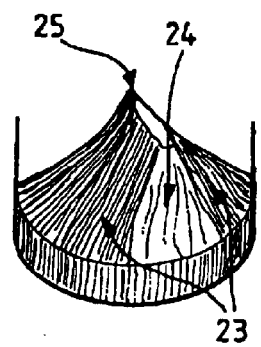
FIG_11b
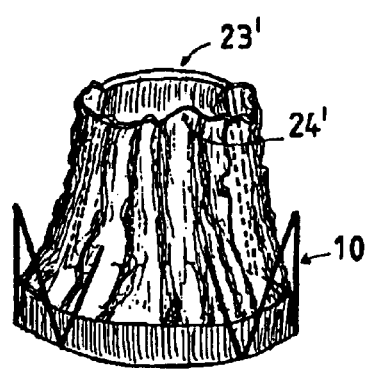
FIG_11c
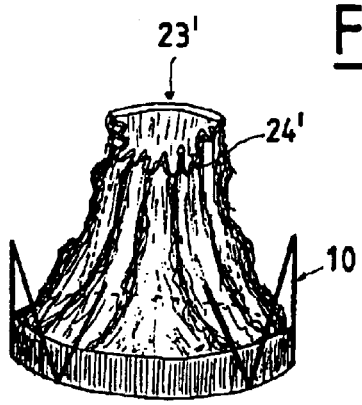
FIG_11d
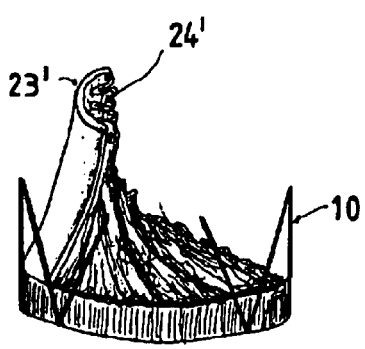
FIG_11e

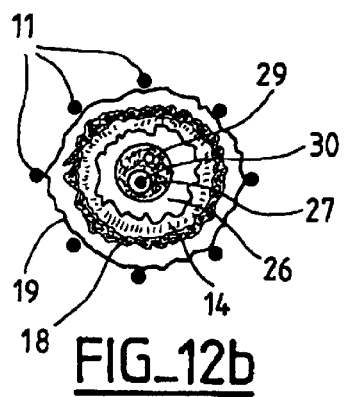
FIG_12b
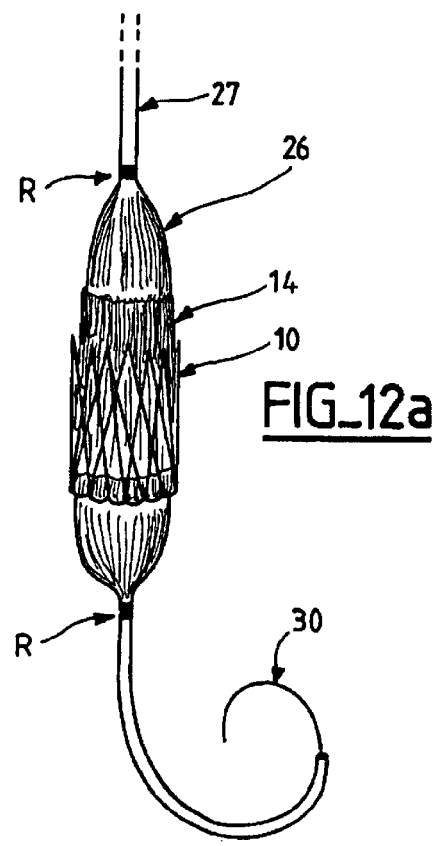
FIG_12a

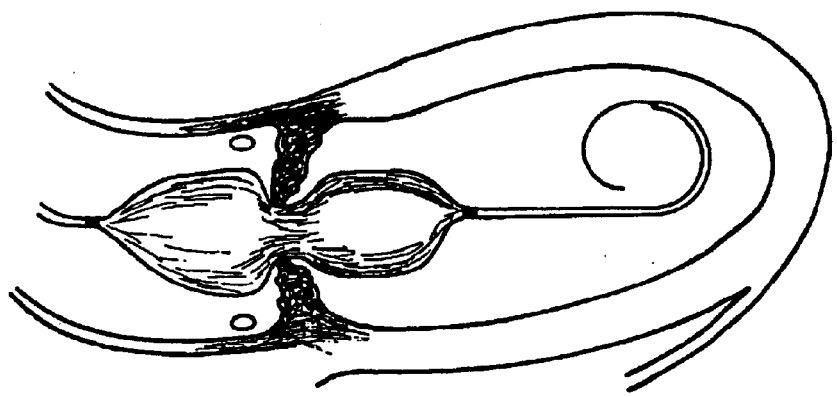
FIG._13c
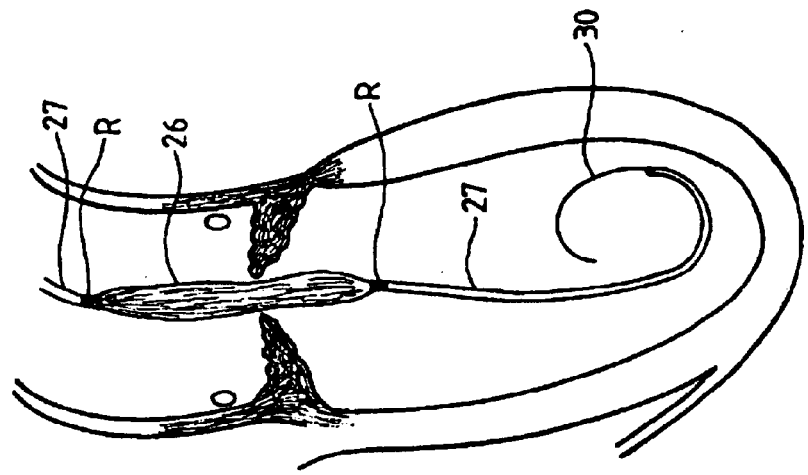
FIG._13b
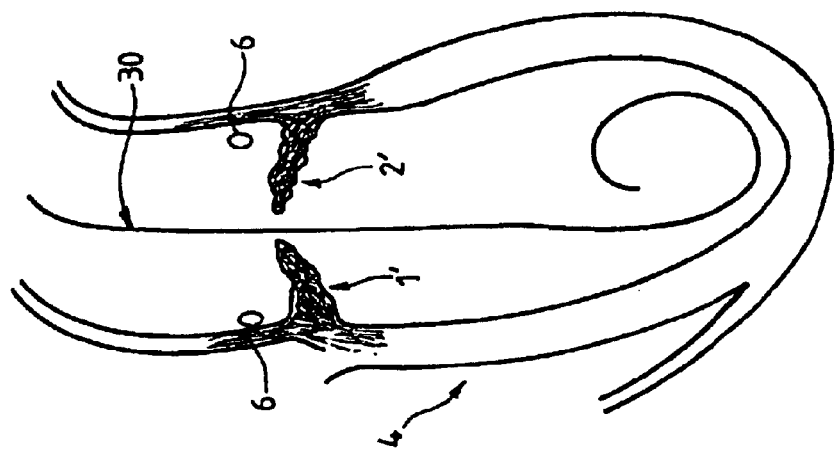
FIG._13a

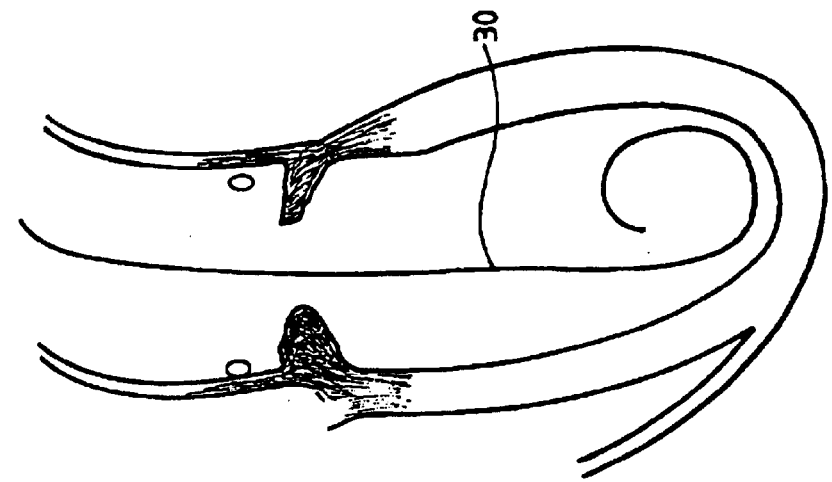
FIG_13f
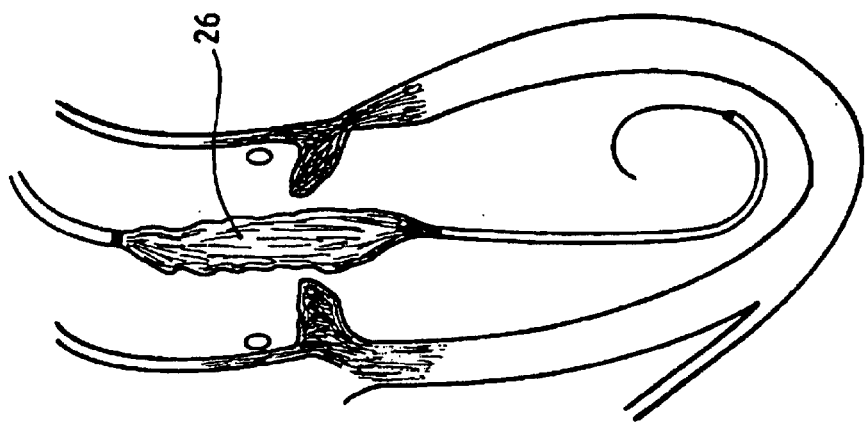
FIG_13e
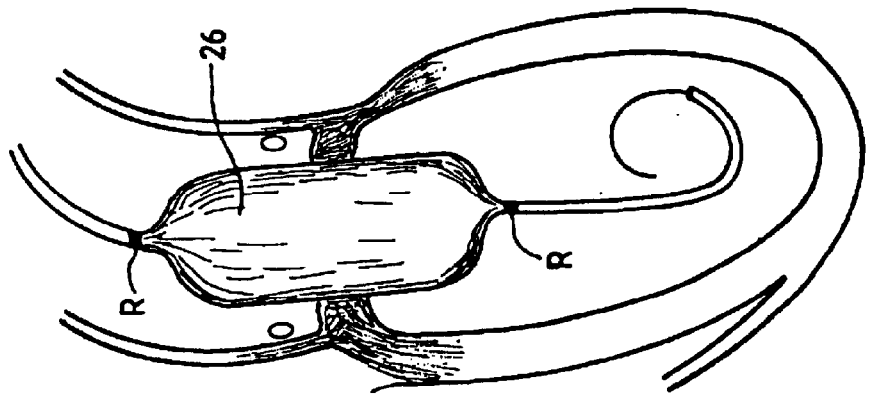
FIG_13d

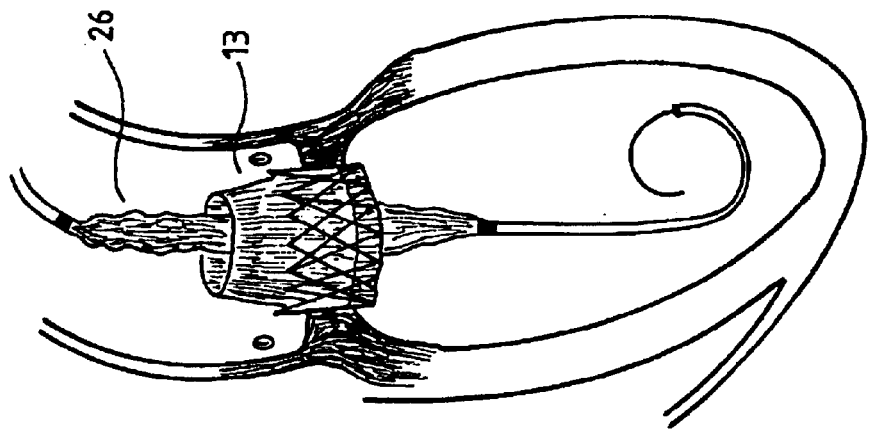
FIG._13i
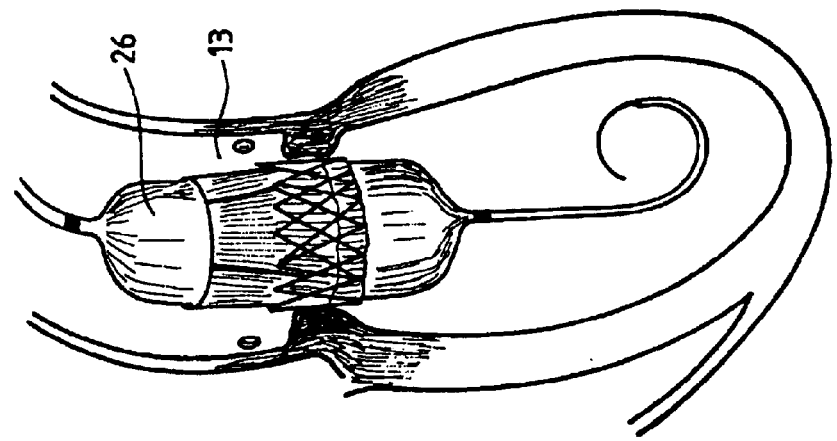
FIG._13h
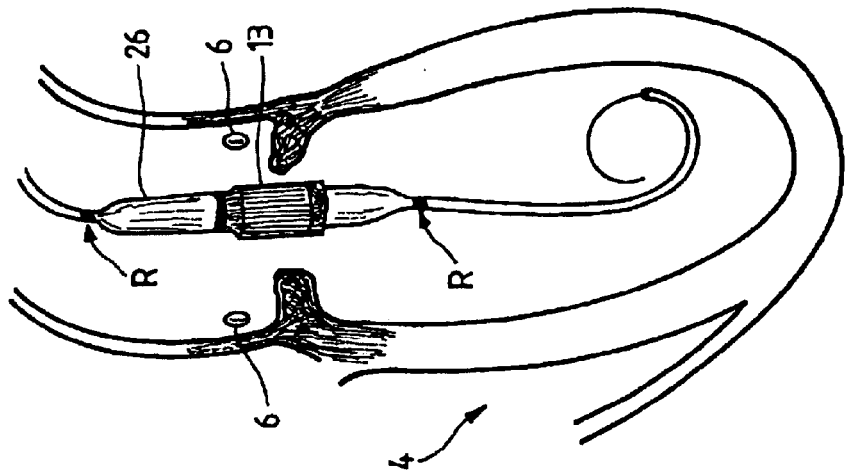
FIG._13g

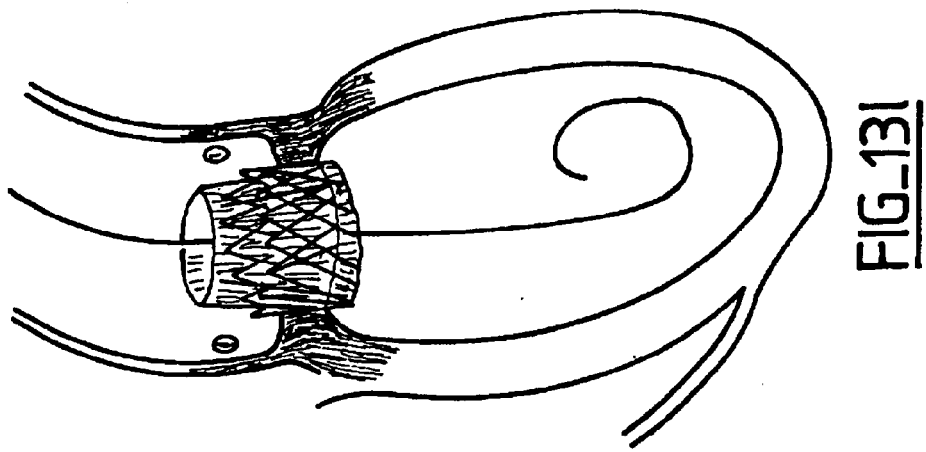
FIG_13l
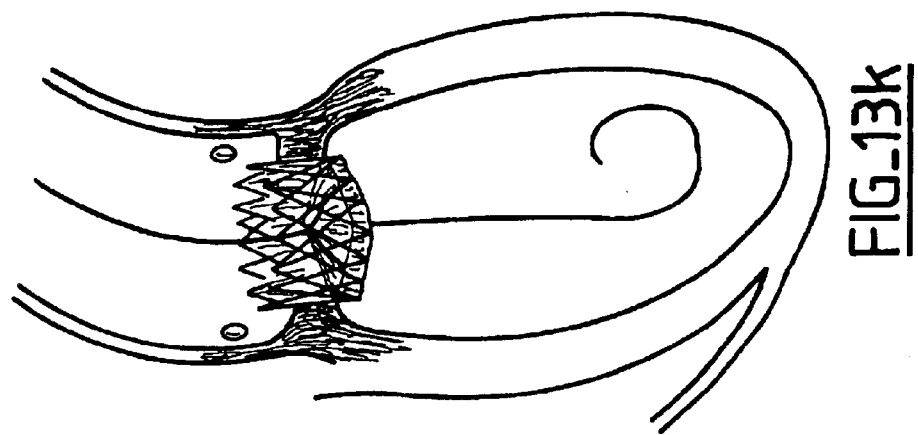
FIG_13k
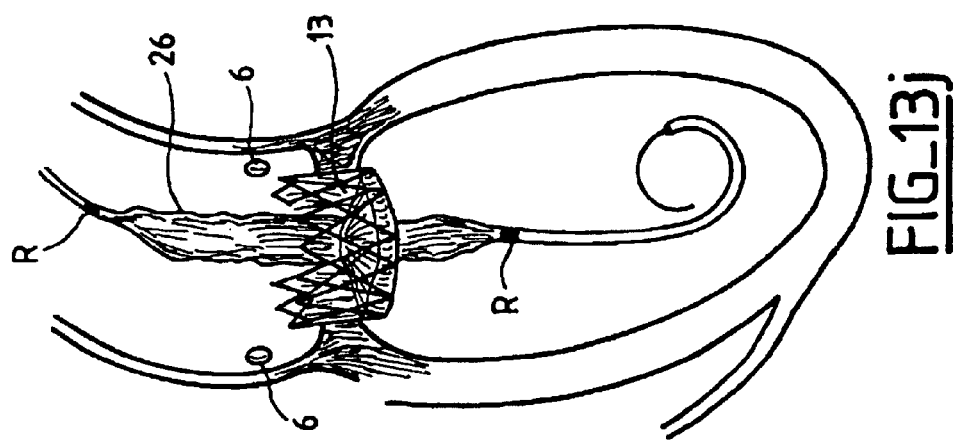
FIG_13j

FIG_14
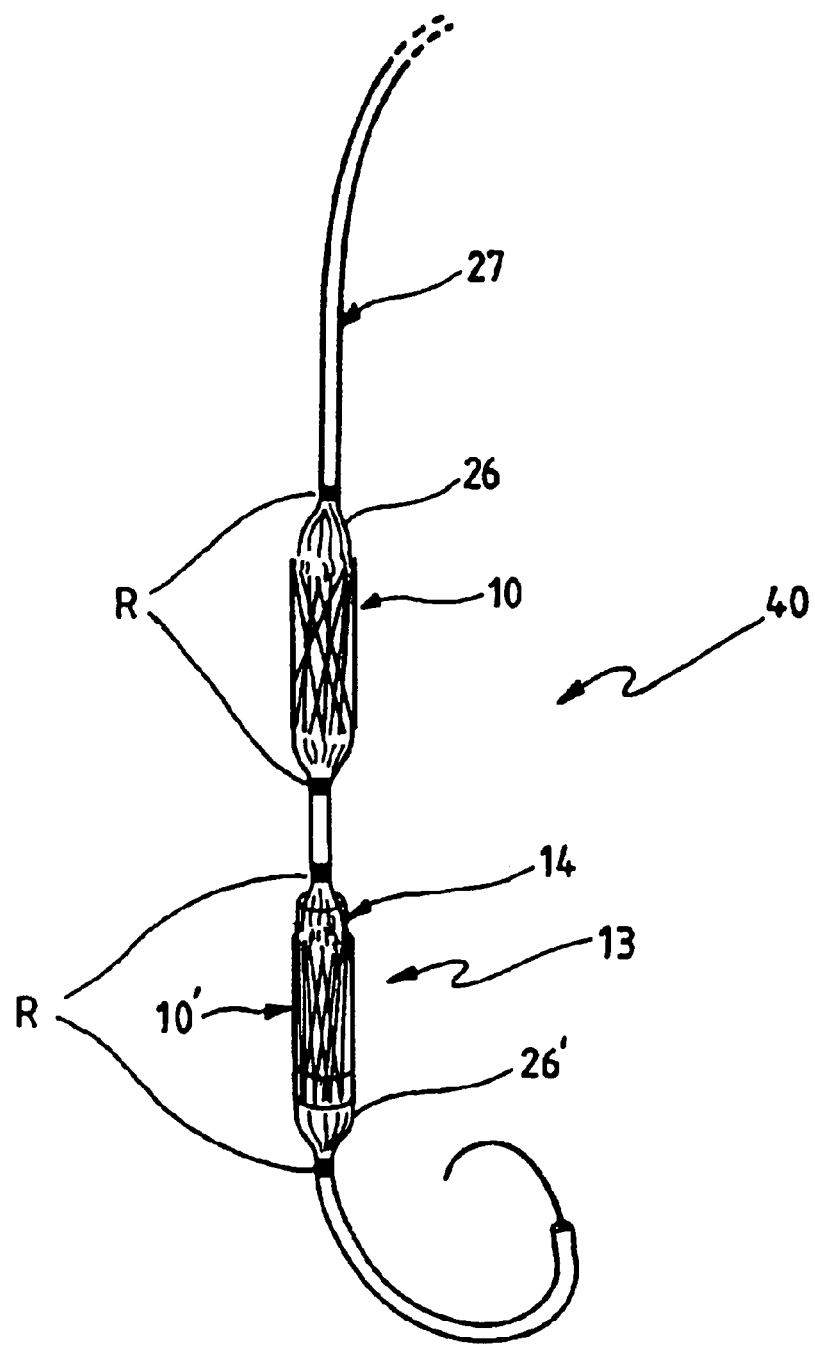

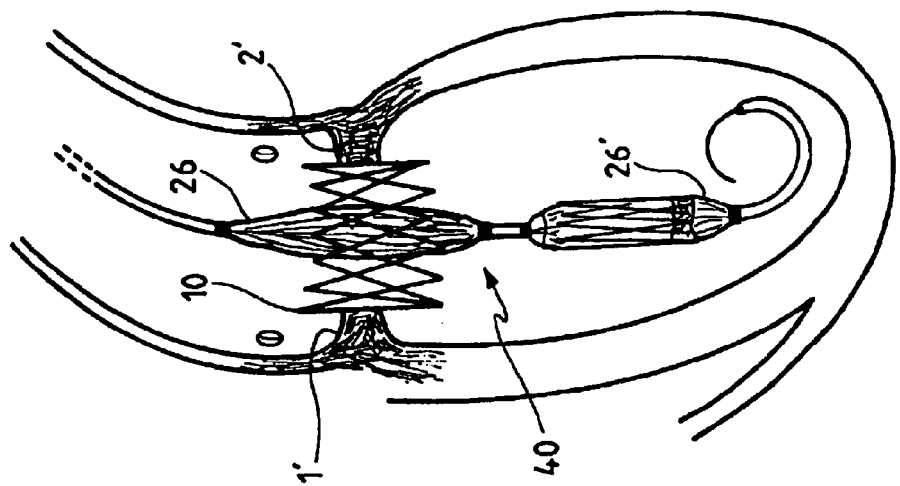
FIG_15c
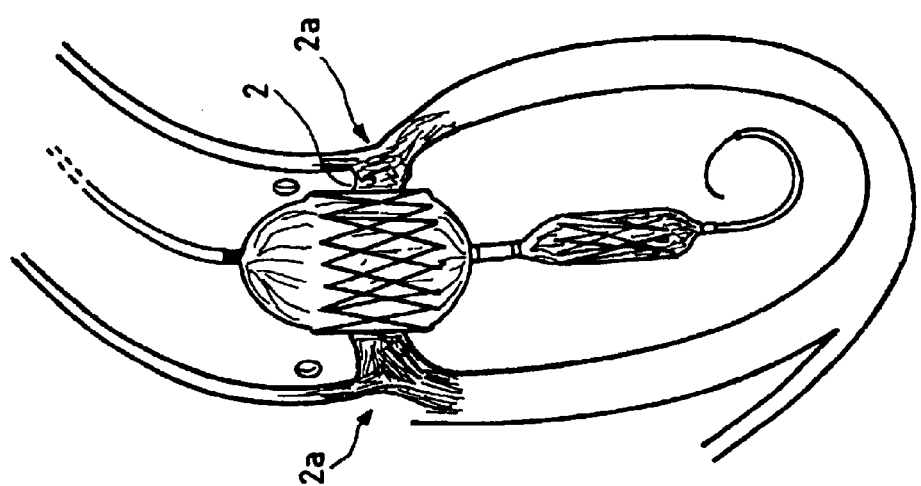
FIG_15b
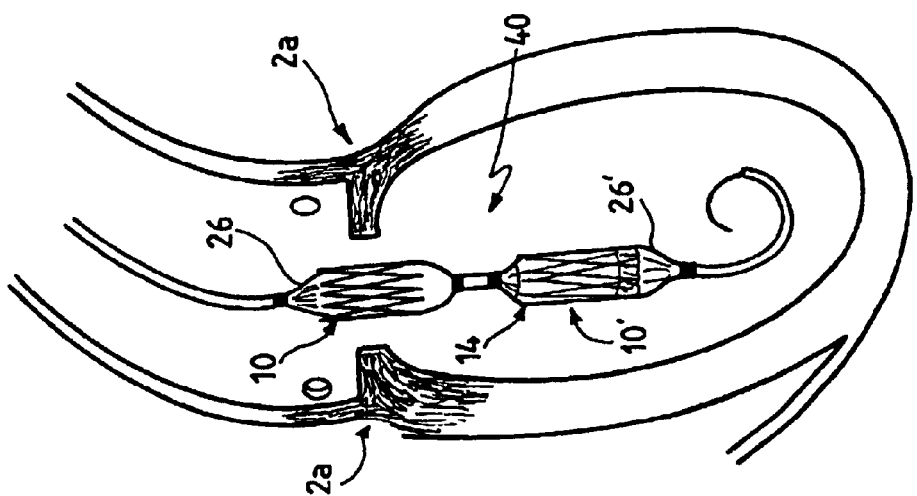
FIG_15a

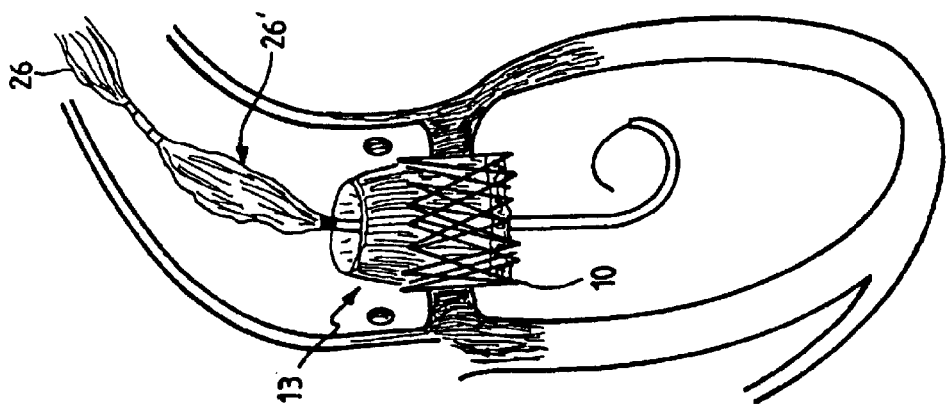
FIG_15f
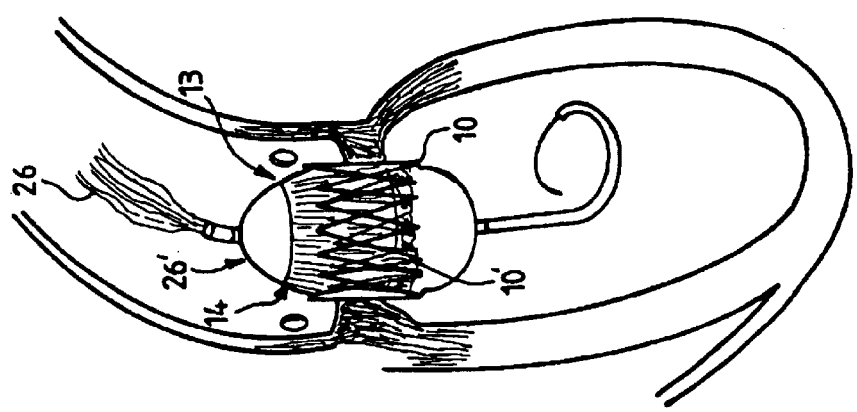
FIG_15e
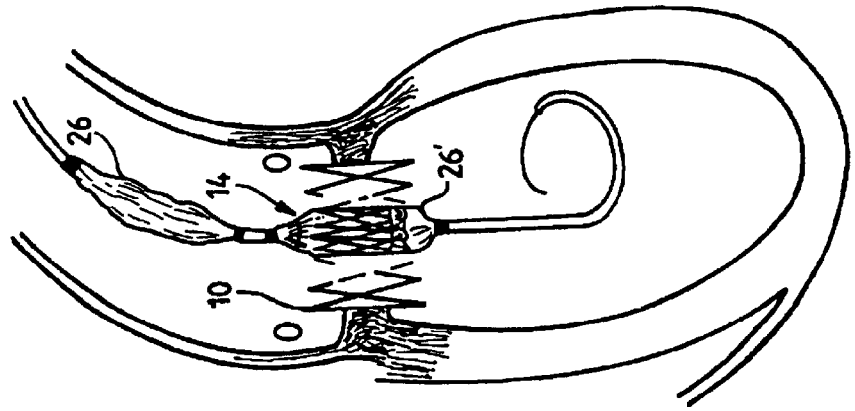
FIG_15d

VALUE PROSTHESIS FOR IMPLANTATION IN BODY CHANNELS

CROSS-REFERENCE TO RELATED APPLICATIONS

This application is a continuation of U.S. patent application Ser. No. 09/795,803, filed Feb. 28, 2001, now abandoned, which in turn is a continuation of U.S. patent application Ser. No. 09/345,824, filed Jun. 30, 1999, now abandoned, which is a National Phase filing of PCT patent application no. PCT/EP97/07337, filed Dec. 31, 1997 and designating the United States, all of which are incorporated herein by reference.

BACKGROUND OF THE INVENTION

The present invention relates to a valve prosthesis for implantation in body channels, more particularly but not only to, cardiac valve prosthesis to be implanted by a transcutaneous catheterization technique.

The valve prosthesis can be also applied to other body channels provided with native valves, such as veins or in organs (liver, intestine, urethra . . . ).

The present invention also relates to a method for implanting a valve prosthesis, such as the valve according to the present invention.

Implantable valves, which will be indifferently designated hereafter as "IV", "valve prosthesis" or "prosthetic valve", permits the reparation of a valvular defect by a less invasive technique in place of the usual surgical valve implantation which, in the case of valvular heart diseases, requires thoracotomy and extracorporeal circulation. A particular use for the IV concerns patients who cannot be operated on because of an associated disease or because of very old age or also patients who could be operated on but only at a very high risk.

Although the IV of the present invention and the process for implanting said IV can be used in various heart valve diseases, the following description will first concern the aortic orifice in aortic stenosis, more particularly in its degenerative form in elderly patients.

Aortic stenosis is a disease of the aortic valve in the left ventricle of the heart. The aortic valvular orifice is normally capable of opening during systole up to 4 to 6 cm$^2$, therefore allowing free ejection of the ventricular blood volume into the aorta. This aortic valvular orifice can become tightly stenosed, and therefore the blood cannot anymore be freely ejected from the left ventricle. In fact, only a reduced amount of blood can be ejected by the left ventricle which has to markedly increase the intra-cavitary pressure to force the stenosed aortic orifice. In such aortic diseases, the patients can have syncope, chest pain, and mainly difficulty in breathing. The evolution of such a disease is disastrous when symptoms of cardiac failure appear, since 50% of the patients die in the year following the first symptoms of the disease.

The only commonly available treatment is the replacement of the stenosed aortic valve by a prosthetic valve via surgery: this treatment moreover providing excellent results. If surgery is impossible to perform, i.e., if the patient is deemed inoperable or operable only at a too high surgical risk, an alternative possibility is to dilate the valve with a balloon catheter to enlarge the aortic orifice. Unfortunately, a good result is obtained only in about half of the cases and there is a high restenosis rate, i.e., about 80% after one year.

Aortic stenosis is a very common disease in people above seventy years old and occurs more and more frequently as the subject gets older. As evidenced, the present tendency of the general evolution of the population is becoming older and older. Also, it can be evaluated, as a crude estimation, that about 30 to 50% of the subjects who are older than 80 years and have a tight aortic stenosis, either cannot be operated on for aortic valve replacement with a reasonable surgical risk or even cannot be considered at all for surgery.

It can be estimated that, about 30 to 40 persons out of a million per year, could benefit from an implantable aortic valve positioned by a catheterization technique. Until now, the implantation of a valve prosthesis for the treatment of aortic stenosis is considered unrealistic to perform since it is deemed difficult to superpose another valve such an implantable valve on the distorted stenosed native valve without excising the latter.

From 1985, the technique of aortic valvuloplasty with a balloon catheter has been introduced for the treatment of subjects in whom surgery cannot be performed at all or which could be performed only with a prohibitive surgical risk. Despite the considerable deformation of the stenosed aortic valve, commonly with marked calcification, it is often possible to enlarge significantly the aortic orifice by balloon inflation, a procedure which is considered as low risk.

However, this technique has been abandoned by most physicians because of the very high restenosis rate which occurs in about 80% of the patients within 10 to 12 months. Indeed, immediately after deflation of the balloon, a strong recoil phenomenon often produces a loss of half or even two thirds of the opening area obtained by the inflated balloon. For instance, inflation of a 20 mm diameter balloon in a stenosed aortic orifice of 0.5 cm$^2$ area gives, when forcefully and fully inflated, an opening area equal to the cross sectional area of the maximally inflated balloon, i.e., about 3 cm$^2$. However, measurements performed a few minutes after deflation and removal of the balloon have only an area around 1 cm$^2$ to 1.2 cm$^2$. This is due to the considerable recoil of the fibrous tissue of the diseased valve. The drawback in this procedure has also been clearly shown on fresh post mortem specimens.

However, it is important to note that whereas the natural normal aortic valve is able to open with an orifice of about 5 to 6 cm$^2$ and to accommodate a blood flow of more that 15 l/min. during heavy exercise for instance, an opening area of about 1.5 to 2 cm$^2$ can accept a 6 to 8 l/min blood flow without a significant pressure gradient. Such a flow corresponds to the cardiac output of the elderly subject with limited physical activity.

Therefore, an IV would not have to produce a large opening of the aortic orifice since an opening about 2 cm$^2$ would be sufficient in most subjects, in particular in elderly subjects, whose cardiac output probably does not reach more than 6 to 8 l/min. during normal physical activity. For instance, the surgically implanted mechanical valves have an opening area which is far from the natural valve opening that ranges from 2 to 2.5 cm$^2$, mainly because of the room taken by the large circular structure supporting the valvular part of the device.

The prior art describes examples of cardiac valves prosthesis that are aimed at being implanted without surgical intervention by way of catheterization. For instance, U.S. Pat. No. 5,411,552 describes a collapsible valve able to be introduced in the body in a compressed presentation and expanded in the right position by balloon inflation.

Such valves, with a semi-lunar leaflet design, tend to imitate the natural valve. However, this type of design is inherently fragile, and such structures are not strong enough to be used in the case of aortic stenosis because of the strong recoil that will distort this weak structure and because they would not be able to resist the balloon inflation performed to position the implantable valve. Furthermore, this valvular structure is attached to a metallic frame of thin wires that will not be able to be tightly secured against the valve annulus. The metallic frame of this implantable valve is made of thin wires like in stents, which are implanted in vessels after balloon dilatation. Such a light stent structure is too weak to allow the implantable valve to be forcefully embedded into the aortic annulus. Moreover, there is a high risk of massive regurgitation (during the diastolic phase) through the spaces between the frame wires which is another prohibitive risk that would make this implantable valve impossible to use in clinical practice.

Furthermore, an important point in view of the development of the IV is that it is possible to maximally inflate a balloon placed inside the compressed implantable valve to expand it and insert it in the stenosed aortic valve up to about 20 to 23 mm in diameter. At the time of maximum balloon inflation, the balloon is absolutely stiff and cylindrical without any waist. At that moment, the implantable valve is squeezed and crushed between the strong aortic annulus and the rigid balloon with the risk of causing irreversible damage to the valvular structure of the implantable valve.

SUMMARY OF THE INVENTION

The invention is aimed to overcome these drawbacks and to implant an IV which will remain reliable for years.

A particular aim of the present invention is to provide an IV, especially aimed at being used in case of aortic stenosis, which structure is capable of resisting the powerful recoil force and to stand the forceful balloon inflation performed to deploy the IV and to embed it in the aortic annulus.

Another aim of the present invention is to provide an efficient prosthesis valve which can be implanted by a catheterization technique, in particular in a stenosed aortic orifice, taking advantage of the strong structure made of the distorted stenosed valve and of the large opening area produced by preliminary balloon inflation, performed as an initial step of the procedure.

A further aim of the present invention is to provide an implantable valve which would not produce any risk of fluid regurgitation.

A further aim of the present invention is to provide a valve prosthesis implantation technique using a two-balloon catheter and a two-frame device.

These aims are achieved according to the present invention which provides a valve prosthesis of the type mentioned in the introductory part and wherein said valve prosthesis comprises a collapsible continuous structure with guiding means providing stiffness and a frame to which said structure is fastened, said frame being strong enough to resist the recoil phenomenon of the fibrous tissue of the diseased valve.

The IV, which is strongly embedded, enables the implantable valve to be maintained in the right position without any risk of further displacement, which would be a catastrophic event.

More precisely, this valvular structure comprises a valvular tissue compatible with the human body and blood, which is supple and resistant to allow said valvular structure to pass from a closed state to an open state to allow a body fluid, more particularly the blood, exerting pressure on said valvular structure, to flow. The valvular tissue forms a continuous surface and is provided with guiding means formed or incorporated within, creating stiffened zones which induce the valvular structure to follow a patterned movement from its open position to its closed state and vice-versa, providing therefore a structure sufficiently rigid to prevent diversion, in particular into the left ventricle and thus preventing any regurgitation of blood into the left ventricle in case of aortic implantation.

Moreover, the guided structure of the IV of the invention allows the tissue of this structure to open and close with the same patterned movement while occupying as little space as possible in the closed state of the valve. Therefore, owing to these guiding means, the valvular structure withstands the unceasing movements under blood pressure changes during the heart beats.

More preferably, the valvular structure has a substantially truncated hyperboloidal shape in its expanded position, with a larger base and a growing closer neck, ending in a smaller extremity forming the upper part of the valvular structure. The valvular structure has a curvature at its surface that is concave towards the aortic wall. Such a shape produces a strong and efficient structure in view of the systolo-diastolic movement of the valvular tissue. Such a valvular structure with its simple and regular shape also lowers the risk of being damaged by forceful balloon inflation at the time of IV deployment.

A trunco-hyperboloidal shape with a small diameter at the upper extremity facilitates the closure of the valve at the beginning of diastole in initiating the starting of the reverse movement of the valvular tissue towards its base. Another advantage of this truncated hyperboloidal shape is that the upper extremity of the valvular structure, because of its smaller diameter, remains at a distance from the coronary ostia during systole as well as during diastole, thus offering an additional security to ensure not to impede at all the passage of blood from the aorta to the coronary ostia.

As another advantageous embodiment of the invention, the guiding means of the valvular structure are inclined strips from the base to the upper extremity of the valvular structure with regard to the central axis of the valvular structure. This inclination initiates and imparts a general helicoidal movement of the valvular structure around said central axis at the time of closure or opening of said structure, such a movement enabling to help initiate and finalize the closure of the valvular structure. In particular, this movement improves the collapse of the valvular structure towards its base at the time of diastole and during the reversal of flow at the very beginning of diastole. During diastole, the valvular structure thus fails down, folding on itself and collapses on its base, therefore closing the aortic orifice. The strips can be pleats, strengthening struts or thickened zones.

In other embodiments, said guiding means are rectilinear strips from the base to the upper extremity of the valvular structure. In this case, the guiding means can comprise pleats, struts or thickened zones. In a particular embodiment, the stiffened zones then created can be advantageously two main portions, trapezoidal in shape, formed symmetrically one to each other with regard to the central axis of the valvular structure, and two less rigid portions separating said two main portions to lead to a tight closeness in shape of a closed slot at the time of closure of the upper extremities of the main portions of the valvular structure. The thickened zones can be extended up to form the stiffened zones.

More particularly, each of said main slightly rigid portions occupy approximately one third of the circumference of the valvular structure when this latter is in its open position. The slightly rigid portions maintain the valvular structure closed during diastole by firmly applying themselves on each other. The closure of the valvular structure at the time of diastole thus does not have any tendency to collapse too much towards the aortic annulus.

Preferably, the guiding means are a number of pleats formed within the tissue by folding, or formed by recesses or grooves made in the tissue. The shape of the pleats is adapted to achieve a global shape of the desired type for said position.

Alternatively, the guiding means are made of strengthening struts, preferably at least three, incorporated in the tissue in combination or not with said pleats.

The guiding means and, in particular, the strengthening struts, help to prevent the valvular tissue from collapsing back too much and to reverse inside the left ventricle through the base of the frame, preventing the risk of blood regurgitation.

In a preferred prosthetic valve of the invention, said valvular tissue is made of synthetic biocompatible material such as TEFLON® or DACRON®, polyethylene, polyamide, or made of biological material such as pericardium, porcine leaflets and the like. These materials are commonly used in cardiac surgery and are quite resistant, particularly to folding movements due to the increasing systolo-diastolic movements of the valvular tissue and particularly at the junction with the frame of the implantable valve.

The valvular structure is fastened along a substantial portion of an expandable frame, by sewing, by molding or by gluing to exhibit a tightness sufficiently hermetical to prevent any regurgitation of said body fluid between the frame and the valvular structure.

Preferably, an internal cover is coupled or is integral to the valvular structure and placed between said valvular structure and the internal wall of the frame to prevent any passage of the body fluid through said frame. Therefore, there is no regurgitation of blood as it would be the case if there were any space between the valvular structure fastened on the frame and the zone of application of the frame on the aortic annulus. The internal cover makes a sort of "sleeve" at least below the fastening of the valvular structure covering the internal surface of the frame and thus prevents any regurgitation of blood through the frame.

In the present invention, the frame is a substantially cylindrical structure capable of maintaining said body channel open in its expanded state and supporting said collapsible valvular structure.

In a preferred embodiment of the invention, the frame is made of a material which is distinguishable from biological tissue to be easily visible by non invasive imaging techniques.

Preferably, said frame is a stainless metal structure or a foldable plastic material, made of intercrossing, preferably with rounded and smooth linear bars. This frame is strong enough to resist the recoil phenomenon of the fibrous tissue of the diseased valve. The size of the bars and their number are determined to give both the maximal rigidity when said frame is expanded and the smallest volume when the frame is compressed.

More preferably, the frame has projecting curved extremities and presents a concave shape. This is aimed at reinforcing the embedding and the locking of the implantable valve in the distorted aortic orifice.

In a preferred embodiment of the present invention, the IV is made in two parts, a first reinforced frame coupled with a second frame which is made of thinner bars than said first frame and which is embedded inside the second frame. This second frame to which the valvular structure is fastened as described above, is preferably less bulky than the first frame to occupy as little space as possible and to be easily expanded using low pressure balloon inflation.

The present invention also relates to a double balloon catheter to separately position the first frame in the dilated stenosed aortic valve and place the second frame that comprises the valvular structure. This catheter comprises two balloons fixed on a catheter shaft and separated by few centimeters.

The first balloon is of the type sufficiently strong to avoid bursting even at a very high pressure inflation and is aimed at carrying, in its deflated state, a strong frame aimed at scaffolding the previously dilated stenosed aortic valve. The second balloon is aimed at carrying the second frame with the valvular structure.

An advantage of this double balloon catheter is that each balloon has an external diameter which is smaller than known balloons since each element to be expanded is smaller.

Moreover, such a double balloon catheter allows to enlarge the choice for making an efficient valvular structure enabling to overcome the following two contradictory conditions:

1) having a soft and mobile valvular structure capable of opening and closing freely in the blood stream, without risk of being damaged by balloon inflation; and
2) needing a very strong structure able to resist the recoil force of the stenosed valve and capable of resisting, without any damage, a strong pressure inflation of the expanding balloon.

Furthermore, the shaft of said double balloon catheter comprises two lumens for successive and separate inflation of each balloon. Of note, an additional lumen capable of allowing a rapid inflation takes additional room in the shaft.

The invention also relates to a method of using a two-balloon catheter with a first frame and second frame to which a valve prosthesis of the type previously described is fastened.

BRIEF DESCRIPTION OF THE DRAWINGS

The invention will now be explained and other advantages and features will appear with reference to the accompanying schematical drawings wherein:

FIGS. 1a, 1b and 1c illustrate, in section views, respectively, the normal aortic valve in systole, in diastole and a stenosed aortic valve;

FIGS. 2a and 2b illustrate two examples of a metallic frame which are combined to a valvular structure according to the present invention;

FIGS. 3a and 3b illustrate a frame according to the invention in its expanded position with an opening out of the extremities, respectively, with a cylindrical and a concave shape;

FIGS. 4a and 4b illustrate an IV of the invention respectively in its compressed position and in its expanded position in an open position as in systole;

FIGS. 5a and 5b illustrate respectively an IV of the invention in its closed position and a sectional view according to the central axis of such a valvular structure which is closed as in diastole;

FIGS. 6a to 6d illustrate a sectional view according to the central axis of an IV according to the present invention and showing the internal cover and the external cover of the valvular structure overlapping partially or non overlapping the frame bars;

FIG. 7 illustrates the frontal zig-zag fastening line of the valvular tissue on the frame;

FIGS. 8a and 8b illustrate, respectively, a perspective view of a valvular structure and an internal cover made all of one piece and a perspective view of the corresponding frame into which they will be inserted and fastened;

FIGS. 9a and 9b illustrate inclined strengthening struts, an example of a valvular structure according to the invention, respectively in the open position and in the closed position;

FIGS. 10a and 10b illustrate an example of a valvular structure comprising pleats, respectively in the open and in the closed position;

FIGS. 11a and 11b illustrate a valvular structure comprising two trapezoidal slightly rigid portions, respectively in the open and in the closed position;

FIGS. 11c to 11e illustrate a valvular structure comprising a rectangular stiffened zone, respectively in the open, intermediate and closed position;

FIGS. 12a and 12b illustrate, respectively, a perspective and cross sectional views of an implantable valve in its compressed presentation squeezed on a balloon catheter;

FIGS. 13a to 13l illustrate views of the successive procedure steps for the IV implantation in a stenosed aortic orifice;

FIG. 14 illustrates an implantable valve made in two parts in its compressed presentation squeezed on a two-balloon catheter with a reinforced frame on a first balloon and with the implantable valve on the second balloon; and FIGS. 15a to 15f illustrate the successive steps of the implantation of the implantation valve in two parts with a two-balloon catheter.

DETAILED DESCRIPTION OF THE PREFERRED EMBODIMENTS

In the diastole and systole illustrations of section views of FIGS. 1a and 1b, the arrows A indicates the general direction of the blood flow. The semi-lunar leaflets 1 and 2 of a native aortic valve (with only two out of three shown here) are thin, supple and move easily from the completely open position (systole) to the closed position (diastole). The leaflets originate from an aortic annulus 2a.

The leaflets 1' and 2' of a stenosed valve as illustrated in FIG. 1c, are thickened, distorted, calcified and more or less fused, leaving only a small hole or a narrow slit 3, which makes the ejection of blood from the left ventricle cavity 4 into the aorta 5 difficult and limited. FIGS. 1a to 1c show also the coronary artery ostium 6a and 6b and FIG. 1a shows, in particular, the mitral valve 7 of the left ventricle cavity 4.

An implantable valve according to the invention essentially comprises a supple valvular structure supported by a strong frame. The positioning of the implantable valve is an important point since the expanded frame has to be positioned exactly at the level of the native valvular leaflets 1, 2 of the native valve, the structures of which are pushed aside by the inflated balloon.

Ideally, the implantable valve is positioned with the fastening line of the valvular structure on the frame exactly on the remains of the crushed stenosed valve to prevent any regurgitation of blood. In practice, it is difficult to position the implantable valve within less than 2 or 3 mm. However, any risk of regurgitation of blood is eliminated with the presence of an internal cover, as will be described below.

The upper limit of the frame should be placed below the opening of the coronary arteries, i.e., the coronary ostia 6, or at their level so that the frame does not impede free blood flow in the coronary arteries. This point is a delicate part of positioning an IV since the distance between the superior limit of the leaflets of the natural valve and the coronary ostia 6 is only about 5 to 6 mm. However, the ostia are located in the Valsalva sinus 8 which constitutes a hollow that are located a little out of the way. This helps to prevent from impeding the coronary blood flow by the IV.

At the time of implantation, the operator evaluates the exact positioning of the coronary ostia by looking at the image produced by a sus-valvular angiogram with contrast injection performed before the implantation procedure. This image will be fixed in the same projection on a satellite TV screen and will permit the evaluation of the level of the origin of the right and left coronary arteries. Possibly, in case the ostia are not clearly seen by sus-valvular angiography, a thin guide wire, as those used in coronary angioplasty, is positioned in each of the coronary arteries to serve as a marker of the coronary ostia.

The lower part of the frame of the IV preferably extends by 2 or 3 mm inside the left ventricle 4, below the aortic annulus 2a. However, this part of the frame should not reach the insertion of the septal leaflet of the mitral valve 7, so that it does not interfere with its movements, particularly during diastole.

FIGS. 2a and 2b show respectively an example of a cylindrical frame or stent 10 comprising intercrossing linear bars 11, with two intersections I by bar 11, the bars 11 being soldered or provided from a folded wire to constitute the frame, with for instance a 20 mm, 15 mm or 12 mm height, and an example with only one intersection of bars 11. Preferably, such a frame is expandable from a size of about 4 to 5 millimeters to a size of about 20 to 25 mm in diameter, or even to about 30–35 mm (or more) in particular cases, for instance for the mitral valve. Moreover, said frame, in its fully expanded state, has a height of approximately between 10 and 15 mm and in its fully compressed frame, a height of approximately 20 mm. The number and the size of the bars are adapted to be sufficiently strong and rigid when the frame is fully open in the aortic orifice to resist the strong recoil force exerted by the distorted stenosed aortic orifice after deflation of the balloon used in the catheterization technique which has been previously maximally inflated to enlarge the stenosed valve orifice.

The frame may have several configurations according to the number of bars 11 and intersections. This number, as well as the size and the strength of the bars 11, are calculated taking into account all the requirements described, i.e., a small size in its compressed form, its capacity to be enlarged up to at least 20 mm in diameter and being strong when positioned in the aortic orifice to be able to be forcefully embedded in the remains of the diseased aortic valve and to resist the recoil force of the aortic annulus. The diameter of the bars is chosen, for instance, in the range of 0.1–0.6 mm.

A frame particularly advantageous presents, when deployed in its expanded state, an opening out 12 at both extremities as shown in FIGS. 3a and 3b, the frame having a linear profile (FIG. 3a) or a concave shape profile (FIG. 3b). This is aimed at reinforcing the embedding of the IV in the aortic orifice. However, the free extremities of the openings 12 are rounded and very smooth to avoid any traumatism of the aorta or of the myocardium.

The structure of a preferred frame used in the present invention both maintains the aortic orifice fully open once dilated and produces a support for the valvular structure. The frame is also foldable. When folded by compression, the diameter of said frame is about 4 to 5 millimeters, in view of its transcutaneous introduction in the femoral artery through an arterial sheath of 14 to 16 F (F means French, a unit usually used in cardiology field) i.e., about 4.5 to 5.1 mm. Also, as described below, when positioned in the aortic orifice, the frame is able to expand under the force of an inflated balloon up to a size of 20 to 23 mm in diameter.

The frame is preferably a metallic frame, preferably made of steel. It constitutes a frame with a grate type design able to support the valvular structure and to behave as a strong scaffold for the open stenosed aortic orifice.

When the frame is fully expanded, its intercrossing bars push against the remains of the native stenosed valve that has been crushed aside against the aortic annulus by the inflated balloon. This produces a penetration and embeds the bars within the remains of the stenosed valve, in particular owing to a concave profile of the frame provided with an opening out, as illustrated in FIG. 3b. This embedding of the frame on the aortic annulus, or more precisely on the remains of the crushed distorted aortic valve, will be determinant for the strong fixation of the IV in the right position, without any risk of displacement.

Moreover, the fact that the valve leaflets in degenerative aortic stenosis are grossly distorted and calcified, sometimes leaving only a small hole or a small slit in the middle of the orifice, has to be considered an advantage for the implantation of the valve and for its stable positioning without risk of later mobilization. The fibrous and calcified structure of the distorted valve provides a strong base for the frame of the IV and the powerful recoil phenomenon that results from elasticity of the tissues contribute to the fixation of the metallic frame.

The height of the fully expanded frame of the illustrated frames 10 is preferably between 10 and 15 mm. Indeed, since the passage from the compressed state to the expanded state results in a shortening of the metallic structure, the structure in its compressed form is a little longer, i.e., preferably about 20 mm length. This does not constitute a drawback for its transcutaneous introduction and its positioning in the aortic orifice.

As mentioned above, the frame is strong enough to be able to oppose the powerful recoil force of the distended valve and of the aortic annulus 2a. Preferably it does not possess any flexible properties. When the frame has reached its maximal expanded shape under the push of a forcefully inflated balloon, it remains substantially without any decrease in size and without any change of shape. The size of the bars that are the basic elements of the frame is calculated in such a way to provide a substantial rigidity when the frame is fully expanded. The size of the bars and their number are calculated to give both maximal rigidity when expanded and the smallest volume when the metallic frame is its compressed position.

At the time of making the IV, the frame is expanded by dilatation to its broadest dimension, i.e., between 20 mm and 25 mm in diameter, so as to be able to fasten the valvular structure on the inside side of its surface. This fastening is performed using the techniques in current use for the making of products such as other prosthetic heart valves or multipolars catheters etc. Afterwards, it is compressed in its minimal size, i.e., 4 or 5 mm, in diameter in view of its introduction in the femoral artery. At time of the IV positioning, the frame is expanded again by balloon inflation to its maximal size in the aortic orifice.

If the frame is built in an expanded position, it will be compressed, after fastening the valvular structure, by exerting a circular force on its periphery and/or on its total height until obtaining the smallest compressed position. If the frame is built in its compressed position, it will be first dilated, for instance, by inflation of a balloon and then compressed again as described above.

To help localizing the IV, the frame being the only visible component of the valve, the shaft of the balloon catheter on which will be mounted the IV before introduction in the body (see below) possesses preferentially metallic reference marks easily seen on fluoroscopy. One mark will be at level of the upper border of the frame and the other at the level of the lower border. The IV, when mounted on the catheter shaft and crimpled on it, is exactly positioned taking into account these reference marks on the shaft.

Accordingly, the frame is visible during fluoroscopy when introduced in the patient's body. When the frame is positioned at the level of the aortic annulus, the upper border of the frame is placed below the coronary ostia. Furthermore, the implanting process during which the balloon inflation completely obstructs the aortic orifice, as seen below, is performed within a very short time, i.e., around 10 to 15 seconds. This also explains why the frame is clearly and easily seen, without spending time to localize it. More particularly, its upper and lower borders are clearly delineated.

FIGS. 4a and 4b show an example of a preferred IV 13 of the present invention, respectively in its compressed position, in view of its introduction and positioning in the aortic orifice, and in its expanded and opened (systole) position. FIGS. 5a and 5b show the expanded position of this example closed in diastole, respectively in perspective and in a crossed section view along the central axis XX of the valve prosthesis.

The valvular structure 14 is compressed inside the frame 10 when this is in its compressed position (FIG. 4a), i.e., it fits into a 4 to 5 mm diameter space. On the other hand, the valvular structure can expand (FIG. 4b) and follow the frame expansion produced by the inflated balloon. It will have to be able to reach the size of the inside of the fully deployed frame.

The illustrated IV 13 is made of a combination of two main parts:
1) the expandible but substantially rigid structure made of the frame 10, a metallic frame in the example; and
2) a soft and mobile tissue constituting the valvular structure 14 exhibiting a continuous surface truncated between a base 15 and an upper extremity 16; the tissue is fastened to the bars 11 of the frame at its base 16 and is able to open in systole and to close in diastole at its extremity 16, as the blood flows in a pulsatile way from the left ventricle towards the aorta.

The tissue has rectilinear struts 17 incorporated in it in plane including the central axis XX, in order to strengthen it, in particular, in its closed state with a minimal occupation of the space, and to induce a patterned movement between its open and closed state. Other examples of strengthening struts are described below. They are formed from thicker zones of the tissue or from strips of stiffening material incorporated in the tissue; they can also beglued or soldered on the valvular tissue.

These strengthening struts help to prevent the valvular tissue from collapsing back too much and to evert inside the left ventricle through the base of the frame. These reinforcements of the valvular tissue help maintain the folded tissue above the level of the orifice during diastole, prevent too much folding back and risk of inversion of the valvular structure inside the left ventricle. By also preventing too much folding, a decrease of the risk of thrombi formation can also be expected by reducing the number of folds.

The truncated shape forming a continuous surface enables to obtain a strong structure and is more efficient for the systolo- diastolic movements of the valvular tissue during heart beats. The truncoidal shape facilitates the closure of the valve structure at the beginning of diastole in facilitating the start of the reverse movement of the valvular tissue towards its base at the time of diastole, i.e., at the time of flow reversal at the very beginning of diastole. During diastole, the valvular structure 14 thus fails down, folding on itself, thereby collapsing on its base, and therefore closing the aortic orifice. In fact, the valvular structure has preferably, as illustrated, an hyperboloid shape, with a curvature on its surface concave towards the aortic wall that will contribute to initiating its closure.

Moreover, the basis of the truncated hyperboloid is fixed on the lower part of a frame and the smallest extremity of the truncated hyperboloid is free in the blood stream, during the respected closing and opening phasis.

An important advantage of this hyperboloidal shape is that the upper extremity 16 of the valvular structure 14 can remain at a distance from the coronary ostia during systole as well as during diastole, because of its smaller diameter, thus offering an additional security to make certain that the passage of blood from aorta to the coronary ostia is not impeded.

The base 15 of the truncated tissue is attached on the frame 10 along a line of coupling 18 disposed between the inferior fourth and the third fourth of the frame in the example. The upper extremity 16, with the smaller diameter, overpasses the upper part of the frame by a few millimeters; 6 to 8 mm, for instance. This gives the valvular structure a total height of about 12 to 15 mm.

The upper extremity 16 of the truncated tissue, i.e., the smaller diameter of the hyperboloidal structure 14, is about 17 to 18 mm in diameter (producing a 2.3 to 2.5 $cm^2$ area opening) for a 20 mm diameter base of the truncated structure, or 19 to 20 mm in diameter (producing a 2.8 or a 3 $cm^2$ area opening) for a 23 mm diameter base. An opening area around 2 $cm^2$ or slightly above, gives satisfactory results, particularly in elderly patients who would not reasonably need to exert high cardiac output.

For instance, in the present example, the line of fastening of the base of the truncated tissue on the frame will have to expand from a 12.5 mm perimeter (for a 4 mm external diameter of the compressed IV) to a 63 mm perimeter (for a 20 mm external diameter of the expanded IV), or to a 72 mm perimeter (for a 23 mm external diameter, in case a 23 mm balloon is used).

Another advantage of this truncated continuous shape is that it is stronger and has less risk of being destroyed or distorted by the forceful balloon inflation at the time of IV deployment. Also, if the truncated hyperboloidal shape is marked, for instance, with a 16 or 17 mm diameter of the upper extremity as compared to a 20 mm diameter of the base (or 18 to 20 mm for 23 mm), the smaller upper part is compliant during balloon inflation in order to enable the balloon to expand cylindrically to its maximal mm diameter (or 23 mm). This is made possible by using a material with some elastic or compliant properties.

The valvular structure of the invention, as shown in the illustrated example, includes advantageously a third part, i.e., the internal cover 19 to be fixed on the internal wall of the frame 10. This internal cover prevents any passage of blood through the spaces between the bars 11 of the frame in case the implantable valve would be positioned with the fastening line of the valvular structure on the frame not exactly on the remains of the dilated aortic valve, i.e., either above or below. It also strengthens the fastening of the valvular structure 14 to the frame 10.

In the different sectional views of the different examples of IV according to the invention, as illustrated at FIGS. 6a to 6c, the internal cover 19 covers the totality of the internal side of the frame 10 (FIG. 6a), only the lower part of the frame 10 (FIG. 6b), or it can additionally cover partially 3 to 5 mm as shown in the passage of blood from aorta to the coronary ostia FIG. 6c, the upper part defined above the coupling line 18 of the valvular structure.

For instance, such an extension of the internal cover 19 above the fastening line 18 of the valvular structure will give another security to avoid any risk of regurgitation through the spaces between the bars 11 in case the IV would be positioned too low with respect to the border of the native aortic valve.

The internal cover can also be molded to the valvular structure or casted to it which therefore constitutes an integral structure. The valvular structure and the internal cover are therefore strongly locked together with minimum risk of detachment of the valvular structure which is unceasingly in motion during systole and diastole. in that case, only the internal cover has to be fastened on the internal surface of the frame which renders the making of the IV easier and makes the complete device stronger and more resistant. In particular, the junction of the mobile part of the valvular structure and the fixed part being molded as one piece is stronger and capable to face the increasing movements during the systolo-diastolic displacements without any risk of detachment.

The presence of the internal cover makes an additional layer of plastic material that occupies the inside of the frame and increases the final size of the IV. Therefore, in the case in which the internal cover is limited to the inferior part of the frame (that is, below the fastening line of the valvular structure), it does not occupy any additional space inside the frame. Here also, it is more convenient and safer to make the valvular structure and this limited internal cover in one piece.

In other aspects, to prevent any regurgitation of blood from the aorta towards the left ventricle during diastole, the base of the valvular structure is preferably positioned exactly at the level of the aortic annulus against the remains of distorted stenosed valve pushed apart by the inflated balloon. Therefore, there is no possibility of blood passage through the spaces between the metallic frame bars 11 below the attachment of the valvular structure.

However, to avoid any risk of leaks, the part of the frame below the fastening of the valvular structure (about 3 to 5 mm) is preferably covered by an internal cover which is preferably made with the same tissue as the valvular structure. Thus, there would be no regurgitation of blood which is a possibility when there is any space between the valvular structure fastened on the metallic frame and the line of application of the frame on the aortic annulus. The internal cover makes a sort of "sleeve" below the fastening of the valvular structure on the internal surface of the frame, covering the spaces between the frame bars of the frame at this level, thus preventing any regurgitation of blood through these spaces.

The internal cover can also have another function, i.e., it can be used to fasten the valvular structure inside the frame, as described below.

At FIG. 6d, the internal cover 19 is extended at its lower end 19' to an external cover 19' which is rolled up to be applied on the external wall of the stent 10. The internal and external cover are molded, glued or soldered to the bars of the stent 10.

The coupling process of the valvular structure on the frame is of importance since it has to be very strong without any risk of detachment of the valvular structure from the frame during millions of heart beats with pulsatile blood flow alternatively opening and closing the valvular structure.

The valvular structure of the invention folds to a very small size inside the frame in the compressed position of the valve and is expandable up to 20 to 23 mm diameter. Also, the valvular structure can resist the strong force exerted by the maximally inflated balloon that will powerfully squeeze it against the bars of the frame or against the internal cover, this one being squeezed directly against the bars of the frame. The junction zone is also particularly subjected to very strong pressure exerted by the inflated balloon. Furthermore, this junction zone must not tear or break off during expansion of the balloon. At this time, each part of the junction zone is squeezed against the bars but nonetheless follows the expansion of the frame.

As shown in FIG. 7, the junction zone is, for example, a fastening line 20 which follows the design of a "zig-zag" line drawn by the intercrossing bars 11 of the frame on the internal cover 19.

The fastening of the valvular structure to the frame can be made by sewing the internal and/or the external cover to the bars. To prevent any leakage of blood, stitches are preferably numerous and very close to each other, either as separated stitches or as a continuous suture line. Also, the stitches are made directly around the bars 11. Furthermore, since the valvular structure is expanded together with the metallic frame, the stitches, if made as a continuous suture line, are also able to expand at the same time.

The fastening process can also be made by molding the base of the valvular structure on the frame. At this level, the bars 11 are imbedded in the coupling line of the valvular structure 14. This mold way also concerns the internal cover 19, when it goes below the coupling line 14 on the frame over few millimeters, for example, 2 to 4 mm. As mentioned above, this is intended in order to prevent any regurgitation of blood just below the lower part of the valvular structure 14 in case the frame 10 would not be exactly positioned on the aortic annulus but at few millimeters away.

The fastening process can further be made by gluing or soldering the valvular structure on the bars with sufficiently powerful biocompatible glues. The same remark can be made concerning the internal cover of the frame below the coupling line of the valvular structure.

Also, this allows the coupling line to follow the frame changes from the compressed position to its expanded one.

The valvular structure can also be fastened on the internal cover previously fixed at the total length of the internal surface of the metallic frame. The internal cover constitutes therefore a surface on which any type of valvular structure be more easily sewed, molded or glued. Because it is a structure with a large surface and is not involved in the movements of the valvular tissue during systole and diastole, the internal cover is more easily fastened to the internal surface of the frame.

In the particular embodiment shown in FIGS. 8a and 8b, the internal cover 19 is fastened, after introduction (indicated by the arrow B), at the upper and lower extremities of the frame 10 on the upper and lower zig-zag lines of the intercrossing bars 11. In fact, the fastening of the internal cover 19 on the zig-zag lines made by the intercrossing bars 11 of the frame allows an easier passage of blood from the aorta above the IV towards the coronary ostia. Indeed, the blood can find more space to flow into the coronary ostia by passing through the lowest point of each triangular space made by two intercrossing bars 11, as indicated by the arrows A1 (see also FIG. 1b).

The fastening of the internal cover 19 on the extremities can be reinforced by various points of attachment on various parts of the internal surface of the frame 10. The internal cover 19 can be fastened by sewing, molding or gluing the bars 11 onto the frame.

Fastening the valvular tissue (and the cover tissue below) on the inside of the frame, requires work on the frame in its expanded position to have access to the inside of this cylindric frame. In a preferred embodiment the frame is expanded a first time for fastening the valvular tissue on its bars, then compressed back to a smaller size to be able to be introduced via arterial introducer and finally expanded again by the balloon inflation.

Since it is aimed at being positioned in the heart after having been introduced by a catheterization technique by a transcutaneous route in a peripheral artery, mainly the femoral artery, the IV should preferably have the smallest possible external diameter. Ideally, it should be able to be introduced in the femoral artery through a 14 F (4,5 mm) size arterial introducer which is the size of the arterial introducer commonly used to perform an aortic dilatation. However, a 16 F (5,1 mm) or even a 18 F (5, 7 mm) introducer would also be acceptable.

Above this size, the introduction of the IV in the femoral artery should probably be done by a surgical technique. This is still quite acceptable since the surgical procedure would be a very light procedure which could be done by a surgeon with a simple local anaesthesia. It has to be recalled that this technique is used to position big metallic frames, about 24 F in size (7.64 mm in diameter), in the abdominal aorta for the treatment of aneurysms of the abdominal aorta. In that situation, this necessitates surgical repair of the artery after withdrawal of the sheath (M. D. Dake, New Engl. J. Med. 1994; 331: 1729–34).

Ideally, an IV should be able to last several tenths of life years without defect, like the mechanical prosthetic valves which are currently implanted by the surgeons. Nevertheless, an implantable valve that would last at least ten years without risk of deterioration would be effective for the treatment of elderly patients.

A valvular structure according to the invention is made of a supple and reinforced tissue which has a thickness to be thin enough to occupy as less as possible space in the compressed form of the valve, is pliable, and also strong enough to stand the unceasing movements under the blood pressure changes during heart beats. The valvular structure is capable of moving from its closed position to its open position under the action of the force exerted by the movements of the blood during systole and diastole, without having any significant resistance to blood displacements.

The material used for the tissue, which exhibits the above mentioned requirements, may be TEFLON® or DACRON®, which are quite resistant to folding movements, at least when they are used to repair cardiac defects such as inter-atrial or interventricular defects or when they are used to repair a valve such as the mitral valve which is subjected to high pressure changes and movements during heart beats. Also, a main point is the increasing systolo-diastolic movements of the valvular tissue, particularly at its junction with the rigid part of the IV, and it is therefore necessary to find the most possible resistant material tissue.

As mentioned previously, the valvular structure can also possibly be made with biological tissue such as the pericardium, or with porcine leaflets, which are commonly used in bioprosthetic surgically implanted valves.

Moreover, the valvular prosthesis of the present invention does not induce any significant thrombosis phenomenon during its stay in the blood flow and is biologically neutral.

To prevent the risk of thrombus formation and of emboli caused by clots, a substance with anti-thrombic properties could be used, such as heparine, ticlopidine, phosphorylcholine, etc., either as a coating material or it can be incorporated into the material used for the implantable valve, in particular, for the valvular structure and/or for the internal cover.

The valvular structure of the invention can have several types of designs and shapes. Besides the example illustrated in FIGS. 4 and 5, examples of strengthened valvular structures according to the invention are shown in FIGS. 9 to 11, respectively in the closed (FIGS. 9a, 10a, 11a) and in the open state (FIGS. 9b, 10b, 11b) to form a prosthetic valve according to the present invention. In those figures, the frame line is simplified to clarify the drawings.

To help initiate and finalize the closure of the valvular structure, four strengthening struts 14a are slightly inclined from the base to the upper part as compared to the central axis XX of the structure, as shown in FIGS. 9a and 9b. Accordingly, a patterned movement of the valvular structure, during the closing and the opening phases, is initiated. This patterned movement is, in the present case, an helicoidal-type one, as suggested in FIGS. 9b and 10b by the circular arrow 21.

FIGS. 10a and 10b illustrate another embodiment to help the closing of the valvular structure and which also involves an helicoidal movement. Represented by lines 22, inclined pleats are formed in the tissue to impart such a movement. As illustrated, these lines have an inclination from the base to the upper part of the valvular structure tissue 14. Pleats are formed by folding the tissue or by alternating thinner and thicker portions. The width and the number of those pleats are variable, and depend particularly on the type of material used. According to another example, these pleats 22 are combined with the above described inclined strengthening struts.

These reinforcing pleats and/or struts, rectilinear or inclined, have the advantage to impart a reproducible movement and, accordingly, to avoid the valvular structure from closing to a nonstructurized collapse on the frame base.

Another shape of the valvular structure comprises two portions: one portion being flexible but with some rigidity, having a rectangular shape, occupying about one third of the circumference of the valvular structure, and the other portion being more supple, flexible and foldable occupying the rest of the circumference at its base as well as at its upper, free border. According to FIG. 11c, this valve is opened, during the ejection of blood, i.e., during systol. In FIG. 11d, a front view of the valve is closed, during an intermediate diastole, and in FIG. 11e the same closed valve during diastole is shown from a side view. The semi-rigid part 24' moves little during systole and during diastole. The foldable part 23' moves away from the rigid part during systole to let the blood flow through the orifice thus made. This orifice, due to the diameter of the upper part which is the same as that of the open stent, is large, generally as large as that of the open stent. At the time of diastole, due to the reverse of pressure, the foldable part moves back towards the semi-rigid part and presses on it, and thus closes the orifice and prevents any regurgitation of blood.

The advantage of such a valve design is to allow a large opening of the upper part of the valvular structure, not only to permit more blood flow at time of systole after the valve has been implanted, but also at the very time of implantation, when the balloon is maximally inflated to expand the valve to imbed it in the valvular annulus. The diameter of the upper part of the valvular structure could be the same size as the balloon, so that there would be no distension of the valvular part of the valve at the time of implantation, and therefore no risk of deterioration of the valvular structure by the inflated balloon.

The foldable part of the valve could be reinforced by strengthening struts to prevent an eversion of the valve towards the left ventricle during diastole.

Another shape of the valvular structure, as illustrated in FIGS. 11a and 11b comprise four portions, alternatively a main portion 23 and a more narrow portion 24. The main and the narrow portions are facing each other. Each portion has an isosceles trapezoidal shape. The main portions 23 are flexible but with some slight rigidity and the more narrow portions 24 are compliant, more supple and foldable. In this type of design, the two slightly rigid main portions 23 maintain the valvular structure closed during diastole by firmly applying on each other in their upper extremities, thus forming a slot-like closure 25. This particular embodiment needs less foldable tissue than in the previous embodiments and the closure of the valvular structure at the time of early diastole does not have any tendency to collapse towards the aortic annulus.

Another design for the valvular structure is a combination of a cylindrical shape followed by a truncated shape.

This type of valvular structure is longer that the hyperboloidal type, for instance, 25 or 30 mm long, therefore exceeding out of the upper part of the metallic frame, by 10 to 20 mm. The cylindrical part corresponds to the 10 metallic frame and remains inside it. The truncated conic shape is the upper part of the valvular structure, totally exceeding out of the upper extremity of the metallic frame. An advantage of such a design is that the balloon can be inflated only in the cylindrical part of the valvular structure, therefore without risk of stretching the truncated conical part of the upper diameter which is smaller than that of the inflated balloon.

When the upper extremity of the cylindrical part has the same size as the lower extremity, there is no difference during balloon inflation in the degree of force exerted by the balloon on the lower and on the upper extremity of the valvular structure. Preferably, rectilinear reinforcing struts are used in this embodiment, to strengthen the valve structure and aid in its shutting without collapsing and inverting inside the left ventricle through the aortic annulus under the force of the diastolic pressure.

Two different processes for implanting a valve according to the present invention are shown respectively in FIGS. 13a to 13l with a unique balloon catheter, as illustrated in FIGS. 12a and 12b and in FIGS. 15a to 15f, with a two-balloon catheter, as illustrated in FIG. 14.

The IV positioning in the aortic orifice and its expansion can be performed with the help of a unique substantially cylindrical balloon catheter 26 in the so-called unique-balloon catheterization technique.

Preparing for its introduction by transcutaneous route in the femoral artery, the IV 13 is, as illustrated in the perspective view of FIG. 10a in a compressed form crimpled on the balloon catheter 26. A central sectional view of the mounted IV 13 on the complete balloon catheter 26 is shown in FIG. 12b.

The shaft 27f of the balloon dilatation catheter 26 is as small as possible, i.e., a 7F (2.2 mm) or a 6 F (1.9 mm) size. The balloon 26 is mounted on the shaft 27 between two rings R. Moreover, the shaft 27 comprises a lumen 28 (FIG. 12b) as large as possible for inflation of the balloon 26 with diluted contrast to allow simple and fast inflation and deflation. It has also another lumen 29 able to accept a stiff guide wire 30, for example 0.036 to 0.038 inches (0.97 mm), to help position the implantable valve with precision.

The balloon 26 has, for example, a 3 to 4 cm length in its cylindrical part and the smallest possible size when completely deflated so that it will be able to be placed inside the folded valve having an outside diameter which ranges between about 4 and 5 mm. Therefore, the folded balloon preferably has at the most a section diameter of about 2.5 to 3 mm.

The balloon is therefore made of a very thin plastic material. It is inflated with saline containing a small amount of contrast dye in such a way to remain very fluid and visible when using X-ray.

However, the balloon 26 has to be sufficiently strong to resist the high pressure that it has to withstand to be capable of expanding the folded valvular structure 14 and the compressed frame in the stenosed aortic orifice considering that, although pre-dilated, the aortic orifice still exerts a quite strong resistance to expansion because of the recoil phenomenon.

This procedure is shown in FIGS. 13a to 13e.

In contrast to the technique used when performing the usual aortic dilatation (without valve implantation), i.e., inflating the balloon maximally markedly above the nominal pressure, if possible, up to the bursting point (which occurs always with a longitudinal tear, without deleterious consequence, and with the advantage of both exerting a maximal dilating force and restoring blood ejection instantaneously), the balloon inflated for expansion of an implantable valve should not burst in any case. Indeed, bursting of the balloon would involve a risk of incomplete valve expansion and wrong positioning. Therefore, the balloon should be very resistant to a very high pressure inflation. Furthermore, the balloon is inflated only up to the nominal pressure indicated by the maker and the pressure is controlled during inflation by using a manometer. Such relatively low pressure should be sufficient since prior to positioning the IV, an efficacious dilatation of the stenosed aortic valve according to the usual technique with a maximally inflated balloon for example 20 mm or 25 mm in size in such a way to soften the distorted valvular tissue and facilitate the enlargement of the opening of the valve at time of IV implantation is performed.

The implantation of the aortic valve 20 can be made in two steps, as described as follows.

The first step, as shown in FIGS. 13a to 13f, consists in introducing the shaft 27 and balloon catheter 26 along the guide wire previously positioned in the ventricle 4 (FIGS. 13a–13b). The dilatation of the stenosed aortic valve 1', 2' using a regular balloon catheter, according to the commonly performed procedure, i.e., with the guide wire 30 introduced in the ventricle 4 (FIG. 13a) and with maximal inflation of the balloon 26 (FIGS. 13c to 13d) up to the bursting point. Dilatation is performed at least with a balloon having about 20 mm diameter, but it can be performed with a balloon having about 23 mm diameter so as to increase maximally the aortic orifice opening before implantation of the valve although the implantable valve is about 20 mm in diameter. This preliminary dilatation of the aortic orifice helps in limiting the force required to inflate the balloon used to expand the implantable valve and position it in the aortic orifice, and also in limiting the recoil of the aortic valve that occurs immediately after balloon deflation. The balloon is deflated (FIG. 13a) and pulled back on the wire guide 30 left inside the ventricle.

Owing to the marked recoil of the stenosed valve and also of the strong aortic annulus, the 20 mm diameter valve is forcefully maintained against the valvular remains at the level of the aortic annulus. Preliminary dilatation has another advantage in that it permits an easier expansion of the IV, having a lower pressure balloon inflation which helps prevent damage of the valvular structure of the IV. This also facilitates the accurate positioning of the prosthetic valve.

The second step corresponds to the implantation of the valve 13 is shown in FIGS. 13g to 13l. The positioning of the IV needs to be precise at a near 2 or 3 mm, since the coronary ostia 6 has to remain absolutely free of any obstruction by the valve 13 (FIGS. 13k and 13l). As mentioned above, this is, for example, performed with the help of the image of the sus-valvular angiogram in the same projection fixed on an adjacent TV screen. The expansion and the positioning of the valve prosthesis 13 is performed within a few seconds (15 to 20 among at most) since during the maximal balloon inflation (which has to be maintained only a very few seconds, 3, 4,) the aortic orifice is obstructed by the inflated balloon 31 and the cardiac output is zero (FIG. 13h). As for the pre-dilatation act itself, the balloon 26 is immediately deflated within less than 5 or 6 seconds (FIG. 13j) and, as soon as the deflation has clearly begun, the closing and opening states of the IV are active whereas the balloon is pulled back briskly in the aorta (FIGS. 13j to 13l). In case the IV is not maximally expanded by the first inflation, it is possible to replace the balloon inside the IV and to reinflate it so as to reinforce the expansion of the IV.

The IV 13 can also be used in aortic regurgitation. This concerns more often younger patients rather than those with aortic stenosis. The contraindication to surgical valve replacement is often not due to the old age of the patients, but stems mainly from particular cases where the general status of the patient is too weak to allow surgery, or because of associated pathological conditions. Apart from the fact that there is no need for a preliminary dilatation, the procedure of the valve implantation remains approximately the same. The balloon inflation inside the IV is chosen accordingly, taking also into account the fact that it is necessary to overdilate the aortic annulus to obtain a recoil phenomenon of the annulus after balloon deflation to help maintain the IV in position without any risk of displacement.

However, the size of the expanded implantable valve is around 25 to 30 mm in diameter, or even bigger, because the aortic annulus is usually enlarged. A preliminary measurement of the annulus will have to be performed on the sus-valvular angiography and by echocardiography to determine the optimal size to choose.

The IV can be used in the mitral position, mainly in case of mitral regurgitation, but also in case of mitral stenosis. Here again, the IV 20 is only described when used only in cases of contraindication to surgical valve repair or replacement. The procedure is based on the same general principles though the route for the valve positioning is different, using the transseptal route, like the commonly performed mitral dilatation procedure in mitral stenosis. The IV size is quite larger than for the aortic localization (about 30 to 35 mm in diameter when expanded or clearly above in case of a large mitral annulus, a frequent occurrence in mitral insufficiency), to be capable of occupying the mitral area. A preliminary measurement of the mitral annulus is performed to determine the optimal implantable valve size to choose. Since the introduction of the IV is performed through a venous route, almost always through the femoral vein which is quite large and distensable, the bigger the size of the IV in its compressed position is not a drawback even if the diameter size is about 6 or 7 mm. Moreover, the problem of protection of the coronary ostia as encountered in the aortic position does not exist here which therefore makes the procedure easier to be performed.

Finally, the IV can be used to replace the tricuspid valve in patients with a tricuspid insufficiency. This procedure is simple to perform since the positioning of the IV is made by the venous route, using the shortest way to place in the right position at the level of the tricuspid orifice practically without any danger from clot migration during the procedure. A large implantable valve is used, with a diameter of about 40 mm or even larger because the tricuspid annulus is often markedly dilated in tricuspid insufficiency. Here also, as in the mitral position, the compressed IV and the catheter used can be without inconvenience, quite larger than that for the aortic position because of the venous route used.

Furthermore, it has to be noted that the IV can be used also as a first step in the treatment of patients who have contraindication to surgery, when they are examined for the first time, but who could improve later on after correction of the initial hemodynamic failure. The IV procedure can be used as a bridge towards surgery for patients in a weak general condition which are expected to improve within the following weeks or months after the IV procedure in such a way that they can be treated by open heart surgery later on. In the same vein, the IV procedure can be used as a bridge towards surgical valve replacement or repair in patients with a profoundly altered cardiac function that can improve secondarily owing to the hemodynamic improvement resulting from the correction of the initial valvular disease by the IV implantation.

Another technique for implantation of an aortic valve by transcutaneous catheterization uses a two-balloon catheter.

An example of this technique using the two parts IV with a two-balloon catheter 40 is shown in FIG. 14.

Two-balloons 26 and 26' are fixed on a unique catheter shaft 27, said balloons being separated by a few millimeters. The two balloons are preferably short, i.e., about 2 to 2.5 cm long in their cylindrical part. The first balloon 26 to be used, carries a first frame 10 aimed at scaffolding the stenosed aortic orifice after initial dilatation. This first balloon 26 is positioned on the aorta side, above the second balloon 26' which is positioned on the left ventricle side. The second balloon 26' carries the expandable valve 13 which is of the type described above made of a second frame 10' and a valvular structure 14 attached to said frame 10'. The difference is that the second frame does not need to be as strong as the first frame and is easier to expand with low balloon pressure inflation which does not risk damaging the valvular structure 14.

This enlarges the choice for making a valvular structure without having to face two contradictory conditions:

1) having a soft and mobile valvular structure 14 capable of opening and closing freely in the blood stream without risk of being damaged by a balloon inflation; and 2) needing a reinforced frame strong enough to be capable of resisting without any damage, a strong pressure inflation of the expanding balloon.

The shaft 27 of this successive two-balloon catheter 40 comprises two lumens for successive and separate inflation of each balloon. Indeed, an additional lumen capable of allowing a fast inflation occupies space in the shaft and therefore an enlargement of the shaft is necessary. However, this enlargement of the shaft stops at the level of the first balloon 26 since, further to said first balloon, only one lumen is necessary to inflate the second balloon 2C, at the level of the IV which is the biggest part of the device.

Another advantage of this two part IV with a two-balloon catheter is that each set of implantable valve and balloon has a smaller external diameter since each element to be expanded, considered separately, is smaller than in combination. This allows obtaining more easily a final device with an external diameter 14F.

The first balloon is sufficiently strong to avoid bursting even at a very high pressure inflation. This first balloon is mounted in the frame in its deflated position, prior to its introduction by the strong frame which is aimed to scaffold the dilated stenosed aortic valve. The size and shape of said frame is comparable to what has been described previously but said frame is calculated (in particular the material, the number and diameter of its bars are chosen by the person skilled in the art) to make sure that it will resist the recoil of the dilated valve and that it will be securely embedded in the remains of the native aortic valve.

The second balloon does not need to be as strong as the first one and, therefore, can be thinner, occupying less space and being easier to expand with a lower pressure for balloon inflation. This second balloon 26' is mounted in the valve itself which, as in the preceding description, comprises a frame to support the valvular structure and said valvular structure.

Also, the second frame 10' does not need to be as strong as the first one. This frame can be slightly shorter, 10 mm instead of 12 mm, and its bars can be thinner. This frame can have an external surface which is a bit rough to allow better fixation on the first frame when expanded. The bars may also have some hooks to fasten to the first frame.

The valvular structure is attached on said second frame and expanded by relatively low pressure in the second balloon called hereafter the IV balloon. It does not need to be as strong as in the preceding case (IV in one part and unique balloon catheter technique) and, therefore, it occupies less space and has less risk to be damaged at the time of expansion.

This technique is shown in FIGS. 15a to 15f.

One of the problems relevant to the IV implantation procedure as described above, with the IV in one part, is the expansion at the same time by the same balloon inflation of both the frame and the valvular structure. Indeed, the frame is a solid element and the valvular structure is a relative weak one that could be damaged when squeezed by the inflated balloon.

Therefore, the valve implantation can be performed in two immediately successive steps. The first step (FIGS. 15a–15b) corresponds to the expansion and the positioning of the first frame with the first balloon 26 wherein inflation is performed at a high pressure. The second step (FIGS. 15d–15e) corresponds to the expansion and the positioning of the valvular structure 14 inside the frame 10' using the second balloon 2C. This second step follows the first one within a few seconds because, in the time interval between the two steps, there is a total aortic regurgitation towards the left ventricle which is an hemodynamic condition that cannot be maintained for more than a few heart beats, i.e., a few seconds, without inducing a massive pulmonary edema and a drop to zero of the cardiac output.

In another embodiment, the first frame to be introduced comprises the valvular structure and the second frame being stronger than the first one to scaffold the previously deleted stenosed aortic valve.

The advantage of this two step procedure would be to allow expansion and positioning of the frame part 10' of the R 13 using strong pressure inflation of the balloon 26' without the risk of damaging the valvular structure 14 which, for its own expansion, would need only light pressure inflation.

The method is schematically detailed in FIGS. 15a to 15f. A previous dilatation of the stenosed aortic valve is performed as an initial step of the procedure to prepare the distorted valve to facilitate the following steps:

1/ positioning the double balloon catheter 40 with the first balloon 26 with the frame at the level of the aortic annulus 2a, the second IV balloon 26' being inside the left ventricle beyond the aortic annulus 2a (FIG. 15a);

2/ compression of the stenosed aortic valve 1', 2' with the first balloon 26 having a 20 mm, preferably with a 23 mm diameter, the balloon being inflated maximally up to the bursting point, to prepare the IV insertion (FIG. 15b). Inflation lasts a few seconds (preferably 10 seconds at most) with powerful pressure being used to expand the frame and forcefully embed said frame in the remains of the dilated valve;

3/ an immediate speedy deflation of said first balloon 26 follows (FIG. 15c); as soon as the balloon 26 is beginning to clearly deflate, the first frame 10 remaining attached to the stenosed valve 1', 2', the catheter is withdrawn to position the IV balloon 26' inside the previously expanded frame 26 (FIG. 15c in which the frame 10' is partially drawn for clarity purpose); and 4/ immediately after being well positioned, the IV balloon 26' is promptly inflated, to expand the IV 13 (FIG. 15c); and/when the IV 13 is blocked inside the first frame 10, the IV balloon 26' is deflated (FIG. 18f).

Finally, the whole device has to be withdrawn to allow homeostasis of the femoral artery puncture hole.

The total duration of the successive steps, particularly the time during which the balloons are inflated, and the time during which the frame is expanded whereas the valve has not yet been positioned and expanded, is about 20 to 30 seconds. This is feasible if the balloons are inflated and deflated within very a few seconds, 6 to 8, for instance. This is permitted if the lumen of the shaft can be sufficiently large, taking into account the inescapable small diameter size of the shaft. This can also be facilitated by a device producing instantaneously a strong inflation or deflation pressure.

I claim:

1. A method of implanting a valve prosthesis to treat valvular aortic stenosis, which comprises the steps of:

(a) advancing a first balloon dilatation catheter having distal and proximal ends and having a deflated first dilatation balloon adjacent the catheter distal end into a patient's vasculature to position said first dilatation balloon within a native stenotic aortic valve and annulus;

(b) inflating said first dilatation balloon to dilate the stenotic aortic valve;

(c) deflating said first dilatation balloon and withdrawing said deflated balloon in the proximal direction;

(d) advancing a second dilatation catheter having distal and proximal ends and having a second deflated dilatation balloon adjacent the catheter distal end, wherein said second balloon has a valve prosthesis arranged circumferentially around said second dilatation balloon, into the patient's vasculature to position said second dilatation balloon and said valve prosthesis adjacent to the previously dilated native stenotic aortic valve;

(e) inflating said second dilatation balloon to cause said valve prosthesis to adhere to said native aortic valve and annulus; and (f) deflating said second dilatation balloon and withdrawing said second catheter in the proximal direction.

2. The method of claim 1, wherein prior to step (a), a guidewire having a distal end is advanced distally into the patient's vasculature until the guidewire distal end is adjacent or distal to the native stenotic aortic valve.

3. The method of claim 2, wherein in steps (a) and (d) the first and second balloon catheters, respectively, are advanced over the guidewire.

4. The method of claim 1, wherein in step (b) the first dilatation balloon is inflated to a high pressure.

5. The method of claim 4, wherein the first dilatation balloon is inflated maximally up to the balloon's bursting point.

6. The method of claim 4, wherein the inflation lasts only a few seconds.

7. The method of claim 1, wherein inflating the dilatation balloon in step (b) tests the native stenotic aortic valve for efficacy of the procedure and creates an aperture in the native stenotic aortic valve.

8. The method of claim 1, wherein in step (e) the second dilatation balloon is inflated to a high pressure.

9. The method of claim 8, wherein the second dilatation balloon is inflated to a pressure less than the pressure to which the first dilatation balloon is inflated.

10. The method of claim 8, wherein the inflation lasts only a few seconds.

11. The method of claim 1, wherein the valve prosthesis needs only a light pressure for its own expansion.

12. The method of claim 1, wherein the valve prosthesis comprises:

a collapsible, elastic valve member comprised of physiologically acceptable material, an elastic stent member in which said valve member is mounted, said stent member having internal and external surfaces, and a support coupled to the valve member and positioned between the valve member and the stent member, wherein said stent member forms a continuous surface and comprises strut members that provide a structure sufficiently rigid to prevent eversion, wherein the support extends from the internal surface of the stent member to the external surface of the stent member, and wherein the stent member has sufficient radial and longitudinal rigidity to withstand the radial force necessary for implantation, to resist aortic recoil forces, and to provide long-term support to the valve structure.

* * * * *

UNITED STATES PATENT AND TRADEMARK OFFICE
CERTIFICATE OF CORRECTION

PATENT NO.      : 6,908,481 B2
APPLICATION NO. : 10/139741
DATED           : June 21, 2005
INVENTOR(S)     : Alain Cribier It is certified that error appears in the above-identified patent and that said Letters Patent is hereby corrected as shown below:

In the Related U.S. Application Data section of the front page of the patent, replace the text "Continuation of application No. 09/795,803, filed on Feb. 28, 2001, now abandoned, which is a continuation of application No. 09/345,824, filed as application No. PCT/EP97/07337 on Dec. 31, 1997, now abandoned.", with the following text: --Continuation of application No. 09/795,803, filed on Feb. 28, 2001, now abandoned, which is a continuation of application No. 09/345,824, filed on Jun. 30, 1999, now abandoned, which is a continuation of international application No. PCT/EP97/07337, filed on Dec. 31, 1997.--.

Column 1, line 10, replace "National Phase filing" with the word --continuation--.

Signed and Sealed this

Tenth Day of June, 2008

JON W. DUDAS
*Director of the United States Patent and Trademark Office*